(12) United States Patent
Sgroi

(10) Patent No.: US 10,743,880 B2
(45) Date of Patent: Aug. 18, 2020

(54) LOADING UNIT LOCKING COLLAR WITH ROTATIONAL ACTUATED RELEASE

(71) Applicant: Covidien LP, Mansfield, MA (US)

(72) Inventor: Anthony Sgroi, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 137 days.

(21) Appl. No.: 15/974,029

(22) Filed: May 8, 2018

(65) Prior Publication Data

US 2018/0256168 A1    Sep. 13, 2018

Related U.S. Application Data

(62) Division of application No. 14/859,590, filed on Sep. 21, 2015, now Pat. No. 9,980,730.

(51) Int. Cl.
*A61B 17/115* (2006.01)
*A61B 17/068* (2006.01)
(Continued)

(52) U.S. Cl.
CPC ........ *A61B 17/1155* (2013.01); *A61B 17/068* (2013.01); *A61B 17/105* (2013.01);
(Continued)

(58) Field of Classification Search
CPC . A61B 17/1155; A61B 17/105; A61B 17/068; A61B 17/162; A61B 2017/00526; A61B 2017/00477; A61B 2017/00473
(Continued)

(56) References Cited

U.S. PATENT DOCUMENTS 1,296,042 A * 3/1919 Bralove ..................... F16B 7/00
                                                        403/379.2
2,110,397 A * 3/1938 Kangas ................. E21B 17/046
                                                        403/326
(Continued)

FOREIGN PATENT DOCUMENTS

CA              908529 A       8/1972
CN           201481477 U       5/2010
(Continued)

OTHER PUBLICATIONS

European Search Report dated May 10, 2016, issued in EP Application No. 15198203.
(Continued)

*Primary Examiner* — Robert F Long
(74) *Attorney, Agent, or Firm* — Carter, DeLuca & Farrell LLP

(57) ABSTRACT

A loading unit includes a shell assembly and a locking collar. The shell assembly has an annular ring that defines a locking slot and a proximal opening. The proximal opening configured to receive a distal end portion of the surgical instrument. The locking collar is rotatably disposed about the annular ring. The locking collar has a body including a flexible tab that has an inwardly extending lock. The locking collar is moveable about the annular ring between a locked and unlocked configuration. In the locked configuration, the lock passes through the locking slot and into the proximal opening of the annular ring. In the unlocked configuration, the body of the locking collar is rotated about the annular ring from the locked configuration to move the lock from within the proximal opening.

16 Claims, 12 Drawing Sheets

(51) Int. Cl.
*A61B 17/10* (2006.01)
*A61B 17/00* (2006.01)
*A61B 17/16* (2006.01)

(52) U.S. Cl.
CPC ... *A61B 17/162* (2013.01); *A61B 2017/00473* (2013.01); *A61B 2017/00477* (2013.01); *A61B 2017/00526* (2013.01)

(58) Field of Classification Search
USPC .... 227/175.1–182.1; 606/139, 153–154, 219
See application file for complete search history.

(56) References Cited

U.S. PATENT DOCUMENTS

| | | | |
|---|---|---|---|
| 3,193,165 A | 7/1965 | Akhalaya et al. | |
| 3,388,847 A | 6/1968 | Kasulin et al. | |
| 3,552,626 A | 1/1971 | Astafiev et al. | |
| 3,638,652 A | 2/1972 | Kelley | |
| 3,656,494 A * | 4/1972 | Cornett | E04H 15/60 135/114 |
| 3,771,526 A | 11/1973 | Rudie | |
| 3,980,805 A * | 9/1976 | Lipari | H01R 24/40 174/88 C |
| 4,183,691 A * | 1/1980 | Van Melle | F16B 2/245 403/108 |
| 4,198,982 A | 4/1980 | Fortner et al. | |
| 4,207,898 A | 6/1980 | Becht | |
| 4,289,133 A | 9/1981 | Rothfuss | |
| 4,304,236 A | 12/1981 | Conta et al. | |
| 4,319,576 A | 3/1982 | Rothfuss | |
| 4,350,160 A | 9/1982 | Kolesov et al. | |
| 4,351,466 A | 9/1982 | Noiles | |
| 4,379,457 A | 4/1983 | Gravener et al. | |
| 4,473,077 A | 9/1984 | Noiles et al. | |
| 4,476,863 A | 10/1984 | Kanshin et al. | |
| 4,485,817 A | 12/1984 | Swiggett | |
| 4,488,523 A | 12/1984 | Shichman | |
| 4,505,272 A | 3/1985 | Utyamyshev et al. | |
| 4,505,414 A | 3/1985 | Filipi | |
| 4,520,817 A | 6/1985 | Green | |
| 4,550,870 A | 11/1985 | Krumme et al. | |
| 4,573,468 A | 3/1986 | Conta et al. | |
| 4,576,167 A | 3/1986 | Noiles | |
| 4,592,354 A | 6/1986 | Rothfuss | |
| 4,603,693 A | 8/1986 | Conta et al. | |
| 4,606,343 A | 8/1986 | Conta et al. | |
| 4,632,290 A | 12/1986 | Green et al. | |
| 4,646,745 A | 3/1987 | Noiles | |
| 4,647,241 A * | 3/1987 | Weber | F16B 7/0426 403/18 |
| 4,665,917 A | 5/1987 | Clanton et al. | |
| 4,667,673 A | 5/1987 | Li | |
| 4,671,445 A | 6/1987 | Barker et al. | |
| 4,700,703 A | 10/1987 | Resnick et al. | |
| 4,703,887 A | 11/1987 | Clanton et al. | |
| 4,708,141 A | 11/1987 | Inoue et al. | |
| 4,717,063 A | 1/1988 | Ebihara | |
| 4,752,024 A | 6/1988 | Green et al. | |
| 4,754,909 A | 7/1988 | Barker et al. | |
| 4,776,506 A | 10/1988 | Green | |
| 4,817,847 A | 4/1989 | Redtenbacher et al. | |
| 4,869,534 A * | 9/1989 | Ketcham | F16L 37/144 285/24 |
| 4,873,977 A | 10/1989 | Avant et al. | |
| 4,893,662 A | 1/1990 | Gervasi | |
| 4,903,697 A | 2/1990 | Resnick et al. | |
| 4,907,591 A | 3/1990 | Vasconcellos et al. | |
| 4,917,114 A | 4/1990 | Green et al. | |
| 4,957,499 A | 9/1990 | Lipatov et al. | |
| 4,962,877 A | 10/1990 | Hervas | |
| 5,005,749 A | 4/1991 | Aranyi | |
| 5,042,707 A | 8/1991 | Taheri | |
| 5,047,039 A | 9/1991 | Avant et al. | |
| 5,104,025 A | 4/1992 | Main et al. | |
| 5,119,983 A | 6/1992 | Green et al. | |
| 5,122,156 A | 6/1992 | Granger et al. | |
| 5,139,513 A | 8/1992 | Segato | |
| 5,158,222 A | 10/1992 | Green et al. | |
| 5,188,638 A | 2/1993 | Tzakis | |
| 5,193,731 A | 3/1993 | Aranyi | |
| 5,197,648 A | 3/1993 | Gingold | |
| 5,197,649 A | 3/1993 | Bessler et al. | |
| 5,205,459 A | 4/1993 | Brinkerhoff et al. | |
| 5,221,036 A | 6/1993 | Takase | |
| 5,222,963 A | 6/1993 | Brinkerhoff et al. | |
| 5,253,793 A | 10/1993 | Green et al. | |
| 5,261,920 A | 11/1993 | Main et al. | |
| 5,271,543 A | 12/1993 | Grant et al. | |
| 5,271,544 A | 12/1993 | Fox et al. | |
| 5,275,322 A | 1/1994 | Brinkerhoff et al. | |
| 5,275,443 A * | 1/1994 | Klinger | F16L 37/144 285/305 |
| 5,282,810 A | 2/1994 | Allen et al. | |
| 5,285,944 A | 2/1994 | Green et al. | |
| 5,285,945 A | 2/1994 | Brinkerhoff et al. | |
| 5,291,910 A * | 3/1994 | Bui | A61H 3/02 135/68 |
| 5,292,053 A | 3/1994 | Bilotti et al. | |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A | 9/1994 | Blanco et al. | |
| 5,350,104 A | 9/1994 | Main et al. | |
| 5,355,897 A | 10/1994 | Pietrafitta et al. | |
| 5,360,154 A | 11/1994 | Green | |
| 5,368,215 A | 11/1994 | Green et al. | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,411,508 A | 5/1995 | Bessler et al. | |
| 5,425,738 A | 6/1995 | Gustafson et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,447,514 A | 9/1995 | Gerry et al. | |
| 5,454,825 A | 10/1995 | Van Leeuwen et al. | |
| 5,464,415 A | 11/1995 | Chen | |
| 5,470,006 A | 11/1995 | Rodak | |
| 5,474,223 A | 12/1995 | Viola et al. | |
| 5,481,949 A * | 1/1996 | Yen | B25B 23/0035 279/24 |
| 5,497,934 A | 3/1996 | Brady et al. | |
| 5,498,042 A * | 3/1996 | Dole | F16L 37/148 285/148.27 |
| 5,503,635 A | 4/1996 | Sauer et al. | |
| 5,522,534 A | 6/1996 | Viola et al. | |
| 5,533,661 A | 7/1996 | Main et al. | |
| 5,560,257 A * | 10/1996 | DeBisschop | B62D 1/192 403/2 |
| 5,588,579 A | 12/1996 | Schnut et al. | |
| 5,609,285 A | 3/1997 | Grant et al. | |
| 5,626,591 A | 5/1997 | Kockerling et al. | |
| 5,632,433 A | 5/1997 | Grant et al. | |
| 5,639,008 A | 6/1997 | Gallagher et al. | |
| 5,641,111 A | 6/1997 | Ahrens et al. | |
| 5,658,300 A | 8/1997 | Bito et al. | |
| 5,669,918 A | 9/1997 | Balazs et al. | |
| 5,685,474 A | 11/1997 | Seeber | |
| 5,709,335 A | 1/1998 | Heck | |
| 5,715,987 A | 2/1998 | Kelley et al. | |
| 5,718,360 A | 2/1998 | Green et al. | |
| 5,720,755 A | 2/1998 | Dakov | |
| 5,727,897 A * | 3/1998 | Liu | A47C 4/18 403/205 |
| 5,732,872 A | 3/1998 | Bolduc et al. | |
| 5,749,896 A | 5/1998 | Cook | |

(56) References Cited

U.S. PATENT DOCUMENTS

| | | | |
|---|---|---|---|
| 5,758,814 A | 6/1998 | Gallagher et al. | |
| 5,799,857 A | 9/1998 | Robertson et al. | |
| 5,814,055 A | 9/1998 | Knodel et al. | |
| 5,833,698 A | 11/1998 | Hinchliffe et al. | |
| 5,836,503 A | 11/1998 | Ehrenfels et al. | |
| 5,839,639 A | 11/1998 | Sauer et al. | |
| 5,855,312 A | 1/1999 | Toledano | |
| 5,860,581 A | 1/1999 | Robertson et al. | |
| 5,868,760 A | 2/1999 | McGuckin, Jr. | |
| 5,881,943 A | 3/1999 | Heck et al. | |
| 5,915,616 A | 6/1999 | Viola et al. | |
| 5,947,363 A | 9/1999 | Bolduc et al. | |
| 5,951,576 A | 9/1999 | Wakabayashi | |
| 5,954,448 A * | 9/1999 | Shim | H01R 33/7664 403/291 |
| 5,957,363 A | 9/1999 | Heck | |
| 5,993,468 A | 11/1999 | Rygaard | |
| 6,024,748 A | 2/2000 | Manzo et al. | |
| 6,030,136 A * | 2/2000 | Bennett | A45D 40/06 401/78 |
| 6,050,472 A | 4/2000 | Shibata | |
| 6,053,390 A | 4/2000 | Green et al. | |
| D425,784 S * | 5/2000 | Beugelsdyk | D8/395 |
| 6,068,636 A | 5/2000 | Chen | |
| 6,083,241 A | 7/2000 | Longo et al. | |
| 6,102,271 A | 8/2000 | Longo et al. | |
| 6,117,148 A | 9/2000 | Ravo et al. | |
| 6,119,913 A | 9/2000 | Adams et al. | |
| 6,126,058 A | 10/2000 | Adams et al. | |
| 6,142,933 A | 11/2000 | Longo et al. | |
| 6,149,667 A | 11/2000 | Hovland et al. | |
| 6,155,610 A | 12/2000 | Godeau et al. | |
| 6,176,413 B1 | 1/2001 | Heck et al. | |
| 6,179,195 B1 | 1/2001 | Adams et al. | |
| 6,193,129 B1 | 2/2001 | Bittner et al. | |
| 6,203,553 B1 | 3/2001 | Robertson et al. | |
| 6,209,773 B1 | 4/2001 | Bolduc et al. | |
| 6,241,140 B1 | 6/2001 | Adams et al. | |
| 6,253,984 B1 | 7/2001 | Heck et al. | |
| 6,254,305 B1 * | 7/2001 | Taylor | B25G 1/04 15/144.4 |
| 6,258,107 B1 | 7/2001 | Balazs et al. | |
| 6,264,086 B1 | 7/2001 | McGuckin, Jr. | |
| 6,269,997 B1 | 8/2001 | Balazs et al. | |
| 6,273,897 B1 | 8/2001 | Dalessandro et al. | |
| 6,279,809 B1 | 8/2001 | Nicolo | |
| 6,302,311 B1 | 10/2001 | Adams et al. | |
| 6,338,737 B1 | 1/2002 | Toledano | |
| 6,343,731 B1 | 2/2002 | Adams et al. | |
| 6,387,105 B1 | 5/2002 | Gifford, III et al. | |
| 6,398,795 B1 | 6/2002 | McAlister et al. | |
| 6,402,008 B1 | 6/2002 | Lucas | |
| 6,439,446 B1 | 8/2002 | Perry et al. | |
| 6,443,973 B1 | 9/2002 | Whitman | |
| 6,450,390 B2 | 9/2002 | Heck et al. | |
| 6,478,210 B2 | 11/2002 | Adams et al. | |
| 6,488,197 B1 | 12/2002 | Whitman | |
| 6,491,201 B1 | 12/2002 | Whitman | |
| 6,494,877 B2 | 12/2002 | Odell et al. | |
| 6,503,259 B2 | 1/2003 | Huxel et al. | |
| 6,517,566 B1 | 2/2003 | Hovland et al. | |
| 6,520,398 B2 | 2/2003 | Nicolo | |
| 6,533,157 B1 | 3/2003 | Whitman | |
| 6,551,334 B2 | 4/2003 | Blatter et al. | |
| 6,578,751 B2 | 6/2003 | Hartwick | |
| 6,585,144 B2 | 7/2003 | Adams et al. | |
| 6,588,643 B2 | 7/2003 | Bolduc et al. | |
| 6,592,596 B1 | 7/2003 | Geitz | |
| 6,601,749 B2 | 8/2003 | Sullivan et al. | |
| 6,605,078 B2 | 8/2003 | Adams | |
| 6,605,098 B2 | 8/2003 | Nobis et al. | |
| 6,612,622 B2 * | 9/2003 | Andre | F16L 33/00 285/305 |
| 6,626,921 B2 | 9/2003 | Blatter et al. | |
| 6,629,630 B2 | 10/2003 | Adams | |
| 6,631,837 B1 | 10/2003 | Heck | |
| 6,632,227 B2 | 10/2003 | Adams | |
| 6,632,237 B2 | 10/2003 | Ben-David et al. | |
| 6,652,542 B2 | 11/2003 | Blatter et al. | |
| 6,659,327 B2 | 12/2003 | Heck et al. | |
| 6,676,671 B2 | 1/2004 | Robertson et al. | |
| 6,681,979 B2 | 1/2004 | Whitman | |
| 6,685,079 B2 | 2/2004 | Sharma et al. | |
| 6,695,198 B2 | 2/2004 | Adams et al. | |
| 6,695,199 B2 | 2/2004 | Whitman | |
| 6,698,643 B2 | 3/2004 | Whitman | |
| 6,716,222 B2 | 4/2004 | McAlister et al. | |
| 6,716,233 B1 | 4/2004 | Whitman | |
| 6,726,697 B2 | 4/2004 | Nicholas et al. | |
| 6,742,692 B2 | 6/2004 | Hartwick | |
| 6,743,244 B2 | 6/2004 | Blatter et al. | |
| 6,763,993 B2 | 7/2004 | Bolduc et al. | |
| 6,769,590 B2 | 8/2004 | Vresh et al. | |
| 6,769,594 B2 | 8/2004 | Orban, III | |
| 6,820,791 B2 | 11/2004 | Adams | |
| 6,821,282 B2 | 11/2004 | Perry et al. | |
| 6,827,246 B2 | 12/2004 | Sullivan et al. | |
| 6,840,423 B2 | 1/2005 | Adams et al. | |
| 6,843,403 B2 | 1/2005 | Whitman | |
| 6,846,308 B2 | 1/2005 | Whitman et al. | |
| 6,852,122 B2 | 2/2005 | Rush | |
| 6,866,178 B2 | 3/2005 | Adams et al. | |
| 6,872,214 B2 | 3/2005 | Sonnenschein et al. | |
| 6,874,669 B2 | 4/2005 | Adams et al. | |
| 6,884,250 B2 | 4/2005 | Monassevitch et al. | |
| 6,905,504 B1 | 6/2005 | Vargas | |
| 6,938,814 B2 | 9/2005 | Sharma et al. | |
| 6,942,675 B1 | 9/2005 | Vargas | |
| 6,945,444 B2 | 9/2005 | Gresham et al. | |
| 6,953,138 B1 | 10/2005 | Dworak et al. | |
| 6,957,758 B2 | 10/2005 | Aranyi | |
| 6,959,851 B2 | 11/2005 | Heinrich | |
| 6,978,922 B2 | 12/2005 | Bilotti et al. | |
| 6,981,941 B2 | 1/2006 | Whitman et al. | |
| 6,981,979 B2 | 1/2006 | Nicolo | |
| 7,032,798 B2 | 4/2006 | Whitman et al. | |
| 7,059,331 B2 | 6/2006 | Adams et al. | |
| 7,059,510 B2 | 6/2006 | Orban, III | |
| 7,077,856 B2 | 7/2006 | Whitman | |
| 7,080,769 B2 | 7/2006 | Vresh et al. | |
| 7,086,267 B2 | 8/2006 | Dworak et al. | |
| 7,114,642 B2 | 10/2006 | Whitman | |
| 7,118,528 B1 | 10/2006 | Piskun | |
| 7,122,044 B2 | 10/2006 | Bolduc et al. | |
| 7,128,748 B2 | 10/2006 | Mooradian et al. | |
| 7,141,055 B2 | 11/2006 | Abrams et al. | |
| 7,168,604 B2 | 1/2007 | Milliman et al. | |
| 7,179,267 B2 | 2/2007 | Nolan et al. | |
| 7,182,239 B1 | 2/2007 | Myers | |
| 7,195,142 B2 | 3/2007 | Orban, III | |
| 7,207,168 B2 | 4/2007 | Doepker et al. | |
| 7,220,237 B2 | 5/2007 | Gannoe et al. | |
| 7,234,624 B2 | 6/2007 | Gresham et al. | |
| 7,235,089 B1 | 6/2007 | McGuckin, Jr. | |
| RE39,841 E | 9/2007 | Bilotti et al. | |
| 7,285,125 B2 | 10/2007 | Viola | |
| 7,303,106 B2 | 12/2007 | Milliman et al. | |
| 7,303,107 B2 | 12/2007 | Milliman et al. | |
| 7,309,341 B2 | 12/2007 | Ortiz et al. | |
| 7,322,994 B2 | 1/2008 | Nicholas et al. | |
| 7,325,713 B2 | 2/2008 | Aranyi | |
| 7,334,718 B2 | 2/2008 | McAlister et al. | |
| 7,335,212 B2 | 2/2008 | Edoga et al. | |
| 7,364,060 B2 | 4/2008 | Milliman | |
| 7,398,908 B2 | 7/2008 | Holsten et al. | |
| 7,399,305 B2 | 7/2008 | Csiky et al. | |
| 7,401,721 B2 | 7/2008 | Holsten et al. | |
| 7,401,722 B2 | 7/2008 | Hur | |
| 7,407,075 B2 | 8/2008 | Holsten et al. | |
| 7,410,086 B2 | 8/2008 | Ortiz et al. | |
| 7,413,366 B2 * | 8/2008 | Bensussan | B25G 1/04 15/145 |
| 7,422,137 B2 | 9/2008 | Manzo | |
| 7,422,138 B2 | 9/2008 | Bilotti et al. | |

(56) References Cited

U.S. PATENT DOCUMENTS

| | | |
|---|---|---|
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,562,442 B2 * | 7/2009 | Montena ............... H01R 43/04 29/751 |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,748,645 B2 * | 7/2010 | Breese ............... A01M 7/005 180/315 |
| 7,770,776 B2 | 8/2010 | Chen et al. |
| 7,771,440 B2 | 8/2010 | Ortiz et al. |
| 7,774,889 B2 * | 8/2010 | Weaver ............... A47L 13/24 15/145 |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,891,343 B2 * | 2/2011 | Braun ............... F02M 55/002 123/446 |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,029,024 B2 * | 10/2011 | Guest ............... F16L 37/101 285/314 |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 * | 2/2012 | Milliman ............... A61B 17/068 227/175.1 |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,328,224 B1 * | 12/2012 | Alsaid ............... B60D 1/52 280/491.2 |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,397,972 B2 * | 3/2013 | Kostrzewski .... A61B 17/07207 227/175.2 |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,590,846 B2 * | 11/2013 | Guthke ............... H02G 3/30 174/74 R |

(56) References Cited

U.S. PATENT DOCUMENTS

| | | | |
|---|---|---|---|
| 8,608,047 B2 | 12/2013 | Holsten et al. | |
| 8,616,428 B2 | 12/2013 | Milliman et al. | |
| 8,616,429 B2 | 12/2013 | Viola | |
| 8,622,275 B2 | 1/2014 | Baxter, III et al. | |
| 8,631,993 B2 | 1/2014 | Kostrzewski | |
| 8,636,187 B2 | 1/2014 | Hueil et al. | |
| 8,640,940 B2 | 2/2014 | Ohdaira | |
| 8,662,370 B2 | 3/2014 | Takei | |
| 8,663,258 B2 | 3/2014 | Bettuchi et al. | |
| 8,672,931 B2 | 3/2014 | Goldboss et al. | |
| 8,678,264 B2 | 3/2014 | Racenet et al. | |
| 8,684,248 B2 | 4/2014 | Milliman | |
| 8,684,250 B2 | 4/2014 | Bettuchi et al. | |
| 8,684,251 B2 | 4/2014 | Rebuffat et al. | |
| 8,684,252 B2 | 4/2014 | Patel et al. | |
| 8,733,611 B2 | 5/2014 | Milliman | |
| 8,875,972 B2* | 11/2014 | Weisenburgh, II | A61B 17/07207 227/176.1 |
| 8,932,362 B2* | 1/2015 | Katrana | A61F 2/3094 623/20.11 |
| 9,113,885 B2* | 8/2015 | Hodgkinson | A61B 17/1114 |
| 9,402,604 B2* | 8/2016 | Williams | A61B 17/07207 |
| 9,506,592 B2* | 11/2016 | Turnau, III | F16L 37/0915 |
| 9,974,540 B2* | 5/2018 | Richard | A61B 17/07207 |
| 9,980,730 B2 | 5/2018 | Sgroi | |
| 10,022,126 B2* | 7/2018 | Sgroi, Jr. | A61B 17/1155 |
| 10,117,656 B2* | 11/2018 | Sgroi, Jr. | A61B 17/1155 |
| 10,278,886 B2* | 5/2019 | Fong | A61H 3/02 |
| 2003/0111507 A1 | 6/2003 | Nunez | |
| 2004/0059227 A1 | 3/2004 | Nita et al. | |
| 2004/0194324 A1* | 10/2004 | Youn-Chyuan | B25B 23/0035 30/337 |
| 2005/0051597 A1 | 3/2005 | Toledano | |
| 2005/0107813 A1 | 5/2005 | Gilete Garcia | |
| 2005/0123344 A1* | 6/2005 | Bensussan | F16B 7/042 403/109.2 |
| 2006/0000869 A1 | 1/2006 | Fontayne | |
| 2006/0011698 A1 | 1/2006 | Okada et al. | |
| 2006/0097025 A1* | 5/2006 | Milliman | A61B 17/115 227/175.1 |
| 2006/0101600 A1* | 5/2006 | Weaver | B25G 3/26 15/145 |
| 2006/0201989 A1 | 9/2006 | Ojeda | |
| 2007/0027473 A1 | 2/2007 | Vresh et al. | |
| 2007/0029363 A1 | 2/2007 | Popov | |
| 2007/0060952 A1 | 3/2007 | Roby et al. | |
| 2008/0179375 A1 | 7/2008 | Scirica | |
| 2008/0308605 A1 | 12/2008 | Scirica | |
| 2009/0236392 A1 | 9/2009 | Cole et al. | |
| 2009/0236398 A1 | 9/2009 | Cole et al. | |
| 2009/0236401 A1 | 9/2009 | Cole et al. | |
| 2009/0326540 A1 | 12/2009 | Estes | |
| 2010/0005931 A1 | 1/2010 | Lai | |
| 2010/0019016 A1 | 1/2010 | Edoga et al. | |
| 2010/0051668 A1 | 3/2010 | Milliman et al. | |
| 2010/0084453 A1 | 4/2010 | Hu | |
| 2010/0147923 A1 | 6/2010 | D'Agostino et al. | |
| 2010/0163598 A1 | 7/2010 | Belzer | |
| 2010/0224668 A1 | 9/2010 | Fontayne et al. | |
| 2010/0230465 A1 | 9/2010 | Smith et al. | |
| 2010/0258611 A1 | 10/2010 | Smith et al. | |
| 2010/0264195 A1 | 10/2010 | Bettuchi | |
| 2010/0327041 A1 | 12/2010 | Milliman et al. | |
| 2011/0011916 A1 | 1/2011 | Levine | |
| 2011/0101066 A1* | 5/2011 | Farascioni | A61B 17/07207 227/175.2 |
| 2011/0114697 A1 | 5/2011 | Baxter, III et al. | |
| 2011/0114700 A1 | 5/2011 | Baxter, III et al. | |
| 2011/0132964 A1* | 6/2011 | Weisenburgh, II | A61B 17/07207 227/176.1 |
| 2011/0142529 A1* | 6/2011 | Oh | A46B 7/04 401/268 |
| 2011/0144640 A1 | 6/2011 | Heinrich et al. | |
| 2011/0147432 A1 | 6/2011 | Heinrich et al. | |
| 2011/0186614 A1 | 8/2011 | Kasvikis | |
| 2011/0192882 A1 | 8/2011 | Hess et al. | |
| 2011/0205072 A1* | 8/2011 | Ben-Mansour | G01M 3/183 340/605 |
| 2011/0276036 A1 | 11/2011 | Spranger et al. | |
| 2012/0061448 A1* | 3/2012 | Zingman | A61B 17/07207 227/175.2 |
| 2012/0083826 A1* | 4/2012 | Chao | A61B 17/00234 606/205 |
| 2012/0116363 A1* | 5/2012 | Houser | A61B 18/1206 606/1 |
| 2012/0145755 A1 | 6/2012 | Kahn | |
| 2012/0193395 A1 | 8/2012 | Pastorelli et al. | |
| 2012/0193398 A1 | 8/2012 | Williams et al. | |
| 2012/0232339 A1 | 9/2012 | Csiky | |
| 2012/0234894 A1* | 9/2012 | Kostrzewski | A61B 17/07207 227/175.2 |
| 2012/0234896 A1* | 9/2012 | Ellerhorst | A61B 17/07207 227/176.1 |
| 2012/0273548 A1 | 11/2012 | Ma et al. | |
| 2012/0273550 A1* | 11/2012 | Scirica | A61B 17/07207 227/176.1 |
| 2012/0325888 A1 | 12/2012 | Qiao et al. | |
| 2013/0015232 A1 | 1/2013 | Smith et al. | |
| 2013/0020372 A1 | 1/2013 | Jankowski et al. | |
| 2013/0020373 A1 | 1/2013 | Smith et al. | |
| 2013/0032628 A1 | 2/2013 | Li et al. | |
| 2013/0056516 A1 | 3/2013 | Viola | |
| 2013/0060258 A1 | 3/2013 | Giacomantonio | |
| 2013/0096591 A1 | 4/2013 | Hart et al. | |
| 2013/0105544 A1 | 5/2013 | Mozdzierz et al. | |
| 2013/0105546 A1 | 5/2013 | Milliman et al. | |
| 2013/0105551 A1 | 5/2013 | Zingman | |
| 2013/0123705 A1 | 5/2013 | Holm et al. | |
| 2013/0126580 A1 | 5/2013 | Smith et al. | |
| 2013/0153630 A1 | 6/2013 | Miller et al. | |
| 2013/0153631 A1 | 6/2013 | Vasudevan et al. | |
| 2013/0153633 A1 | 6/2013 | Casasanta, Jr. et al. | |
| 2013/0153634 A1* | 6/2013 | Carter | A61B 17/072 227/176.1 |
| 2013/0153638 A1 | 6/2013 | Carter et al. | |
| 2013/0153639 A1* | 6/2013 | Hodgkinson | A61B 17/1114 227/180.1 |
| 2013/0175315 A1 | 7/2013 | Milliman | |
| 2013/0175318 A1 | 7/2013 | Felder et al. | |
| 2013/0175319 A1 | 7/2013 | Felder et al. | |
| 2013/0175320 A1 | 7/2013 | Mandakolathur Vasudevan et al. | |
| 2013/0181029 A1 | 7/2013 | Milliman | |
| 2013/0181035 A1 | 7/2013 | Milliman | |
| 2013/0181036 A1 | 7/2013 | Olson et al. | |
| 2013/0186930 A1 | 7/2013 | Wenchell et al. | |
| 2013/0193185 A1 | 8/2013 | Patel | |
| 2013/0193187 A1 | 8/2013 | Milliman | |
| 2013/0193190 A1 | 8/2013 | Carter et al. | |
| 2013/0193191 A1 | 8/2013 | Stevenson et al. | |
| 2013/0193192 A1 | 8/2013 | Casasanta, Jr. et al. | |
| 2013/0200131 A1* | 8/2013 | Racenet | A61B 17/072 227/180.1 |
| 2013/0206816 A1 | 8/2013 | Penna | |
| 2013/0214027 A1 | 8/2013 | Hessler et al. | |
| 2013/0214028 A1 | 8/2013 | Patel et al. | |
| 2013/0228609 A1 | 9/2013 | Kostrzewski | |
| 2013/0240597 A1 | 9/2013 | Milliman et al. | |
| 2013/0240600 A1 | 9/2013 | Bettuchi | |
| 2013/0248581 A1 | 9/2013 | Smith et al. | |
| 2013/0277411 A1 | 10/2013 | Hodgkinson et al. | |
| 2013/0277412 A1 | 10/2013 | Gresham et al. | |
| 2013/0284792 A1 | 10/2013 | Ma | |
| 2013/0292449 A1 | 11/2013 | Bettuchi et al. | |
| 2013/0299553 A1 | 11/2013 | Mozdzierz | |
| 2013/0299554 A1 | 11/2013 | Mozdzierz | |
| 2013/0306701 A1 | 11/2013 | Olson | |
| 2013/0306707 A1 | 11/2013 | Viola et al. | |
| 2014/0008413 A1 | 1/2014 | Williams | |
| 2014/0012317 A1 | 1/2014 | Orban et al. | |
| 2014/0309677 A1 | 10/2014 | Baldwin | |

(56) References Cited

U.S. PATENT DOCUMENTS

| | | | | |
|---|---|---|---|---|
| 2014/0312095 | A1* | 10/2014 | Scirica | A61B 17/068 227/176.1 |
| 2015/0108201 | A1* | 4/2015 | Williams | A61B 17/068 227/177.1 |
| 2015/0320420 | A1* | 11/2015 | Penna | A61B 17/072 227/176.1 |
| 2015/0351769 | A1* | 12/2015 | Lee | A61B 17/1155 227/179.1 |
| 2015/0374371 | A1* | 12/2015 | Richard | A61B 17/07207 227/176.1 |
| 2016/0000428 | A1* | 1/2016 | Scirica | A61B 1/32 227/180.1 |
| 2016/0157856 | A1* | 6/2016 | Williams | A61B 17/068 227/175.1 |
| 2016/0175026 | A1* | 6/2016 | Bhagat | A61B 17/29 606/52 |
| 2016/0192938 | A1* | 7/2016 | Sgroi, Jr. | A61B 17/1155 227/175.1 |
| 2016/0192939 | A1* | 7/2016 | Sgroi, Jr. | A61B 17/1155 227/176.1 |
| 2017/0020526 | A1* | 1/2017 | Scirica | A61B 17/105 |
| 2017/0079660 | A1* | 3/2017 | Sgroi | A61B 17/105 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1190796 A1 | 3/2002 |
| EP | 1354560 A2 | 10/2003 |
| EP | 1631199 A1 | 3/2006 |
| EP | 2090245 A1 | 8/2009 |
| EP | 2524656 A2 | 11/2012 |
| EP | 2774549 A2 | 9/2014 |
| EP | 3042619 A1 | 7/2016 |
| FR | 1136020 A | 5/1957 |
| FR | 1461464 A | 2/1966 |
| FR | 1588250 A | 4/1970 |
| FR | 2243758 A1 | 4/1975 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 9805261 A2 | 2/1998 |
| WO | 0154594 A1 | 8/2001 |
| WO | 2004107990 A1 | 12/2004 |
| WO | 2008107918 A1 | 9/2008 |
| WO | 2012015917 A1 | 2/2012 |
| WO | 2014139327 A1 | 9/2014 |
| WO | 2014139440 A1 | 9/2014 |
| WO | 2014139442 A1 | 9/2014 |
| WO | 2014139467 A1 | 9/2014 |
| WO | 20140139442 A1 | 9/2014 |

OTHER PUBLICATIONS

European Search Report dated May 17, 2016, issued in EP Application No. 16150284.
European Search Report dated Jun. 24, 2016, issued in EP Application No. 16150288.5.
European Search Report dated Sep. 1, 2016, issued in EP 16166326.
Partial European Search Report dated Jan. 16, 2017, issued in EP Appln. No. 16180339.
European Search Report dated Nov. 30, 2016, issued in EP Application No. 16181395.
European Search Report dated May 23, 2017, issued in EP Application No. 16189648.
EP Examination Report dated Jun. 20, 2017, issued in EP Application No. 16150288.
Australian Office Action dated May 19, 2020, issued in AU Appln. No. 2016219576, 4 pages.
Chinese Office Action dated May 26, 2020, issued in CN Appln. No. 201610834743.

* cited by examiner

LOADING UNIT LOCKING COLLAR WITH ROTATIONAL ACTUATED RELEASE

CROSS-REFERENCE TO RELATED APPLICATIONS

The present application is a Divisional Application which claims that benefit of and priority to U.S. patent application Ser. No. 14/859,590, filed on Sep. 21, 2015, the entire content of which is incorporated herein by reference.

BACKGROUND

1. Technical Field

The present disclosure relates generally to surgical stapling instruments. More specifically, the present disclosure relates to circular surgical stapling instruments including replaceable loading units.

2. Background of Related Art

Surgical stapling instruments configured to join tissue portions during a surgical procedure are well known. These instruments include linear end effectors which are oriented parallel or transverse to a longitudinal axis of the instrument as well as circular end effectors. Typically, linear stapling instruments include a disposable loading unit or a replaceable cartridge that allows the stapling instrument to be used multiple times. However, conventional circular stapling instruments include a cartridge or shell assembly that is typically fixedly attached to the instrument such that the instrument must be disposed of after a single use. Some circular stapling instruments include a cartridge or shell assembly that is replaceable.

A need exists in the art for a simple, inexpensive instrument for releasably securing a cartridge or shell assembly to a circular stapling instrument to facilitate reuse of the stapling instrument.

SUMMARY

In an aspect of the present disclosure, a loading unit includes a shell assembly and a locking collar. The shell assembly has an annular ring that defines a proximal opening that is configured to receive a distal end portion of a surgical instrument. The annular ring defines a locking slot. The locking collar is rotatably disposed about the annular ring and has a body including a flexible tab. The flexible tab includes a lock extending inwardly from the flexible tab. The locking collar is moveable about the annular ring between a locked configuration and an unlocked configuration. In the locked configuration the lock passes through the locking slot and into the proximal opening of the annular ring. In the unlocked configuration the lock is moved from within the proximal opening. The body may be partially split to form the flexible tab.

In aspects, an outer surface of the annular ring defines a groove and the locking collar includes an inwardly extending travel rib that is received within the groove. The travel rib may limit a degree of rotation of the locking collar about the annular ring.

In some aspects, the loading unit includes a retention ring that is positioned about the annular ring proximal of the locking collar to prevent axial movement of the locking collar from relative to the annular ring. The retention ring may include a plurality of inwardly extending retention tabs and the annular ring may define a plurality of retention slots positioned proximally of the locking slot. Each of the plurality of retention slots may be configured to receive a respective retention tab to fix the retention ring to the annular ring.

In certain aspects, the flexible tab is resilient and is positioned to urge the locking collar to the locked configuration. The lock may have a longitudinal cam surface and a radial cam surface. The radial cam surface may be positioned to engage the annular ring to move the lock outward in response to rotation of the body of the locking collar in relation to the annular ring towards the unlocked configuration. The radial cam surface may be positioned to engage the annular ring such that resiliency of the flexible tab causes the radial cam surface to urge the locking collar towards the locked configuration when the lock and the locking slot are misaligned.

In another aspect of the present disclosure, a surgical system includes a surgical instrument, a loading unit, and a locking collar. The surgical instrument includes a distal end portion that defines a locking window. The loading unit includes a shell assembly having an annular ring defining a proximal opening and a locking slot. The distal end portion of the surgical instrument is received within the proximal opening. The locking collar is rotatably disposed about the annular ring to secure the loading unit to the distal end portion of the surgical instrument. The locking collar has a body that includes a flexible tab. The flexible tab has a lock that extends inward from the flexible tab. The locking collar is moveable about the annular ring between a locked configuration and an unlocked configuration. In the locked configuration the lock passes through the locking slot of the annular ring and the locking window of the distal end portion of the surgical instrument to secure the locking collar to the distal end portion of the surgical instrument. In the unlocked configuration the lock is moved from within the locking window to release the loading unit from the distal end portion of the surgical instrument.

In aspects, the annular ring includes a key that extends into the proximal opening. The distal end portion of the surgical instrument may define a keyway. The key is parallel to a longitudinal axis of the shell assembly and the keyway is parallel to a longitudinal axis of the distal end portion of the surgical instrument. The key is received within the keyway to rotatably fix the loading unit to the distal end portion of the surgical instrument.

In some aspects, the lock has a longitudinal cam surface. A distal end of the surgical instrument may be configured to engage the longitudinal cam surface to move the lock outward as the distal end portion of the surgical instrument is received within the proximal opening until the locking window is aligned with the locking slot of the annular ring. The lock may have radial cam surface that engages the annular ring in response to rotation of the body of the locking collar about the annular ring to transition the locking collar to the unlocked configuration.

In another aspect of the present disclosure, a method of securing a loading unit to a surgical instrument includes aligning a proximal annular ring of the loading unit with a distal end portion of the surgical instrument, sliding the annular ring over the distal end portion of the surgical instrument, and continuing to slide the loading unit over the distal end portion until a locking window defined in the distal end portion of the surgical instrument is aligned with a lock such that resilience of a flexible tab move the lock into the locking window to secure the loading unit to the surgical instrument. The distal end of the surgical instrument engages the lock of the locking collar as the annular ring is slid over the distal end portion of the surgical instrument.

In aspects, the method includes releasing the loading unit from the distal end portion of the surgical instrument. The loading unit is released by rotating the locking collar about the annular ring to move the lock from within the locking window and sliding the loading unit off of the distal end portion of the surgical instrument. Rotating the locking collar about the annular ring may engage a radial cam surface of the lock with the annular ring to lift the lock from within the locking window. The locking collar may be released after sliding the loading unit off of the distal end portion of the surgical instrument such that the radial cam surface engages the annular ring to rotate the locking collar about the annular ring in response to residence of the flexible tab.

In some aspects, aligning the proximal ring of the loading unit with the distal end portion of the surgical instrument includes radially aligning a key of the loading unit with a keyway defined in the distal end portion of the surgical instrument. Sliding the annular ring over the distal end portion of the surgical instrument may include sliding the key into the keyway of the surgical instrument.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION OF EMBODIMENTS

Figure 1A:
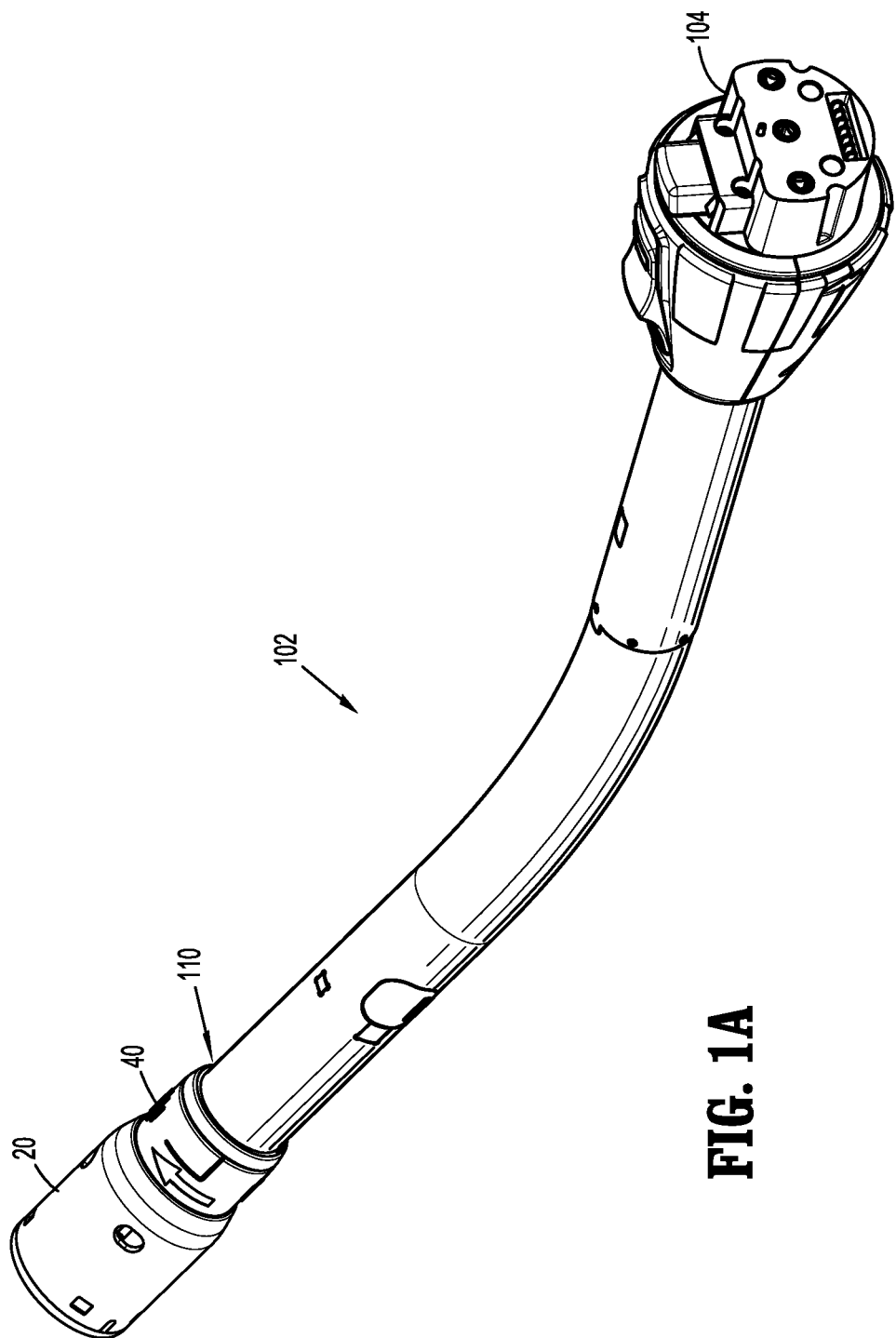
FIG. 1A is a perspective view of a circular stapling adapter with a loading unit releasably coupled in accordance with the present disclosure to a distal end of the circular stapling adapter.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

This disclosure relates generally to a loading unit including a locking collar that releasably secures the loading unit to a distal end of a surgical instrument or adapter for a surgical instrument. The locking collar is rotatably disposed about the loading unit and includes a lock that has a longitudinal cam surface and a radial cam surface. The longitudinal cam surface is engaged by a distal end of the surgical instrument as the locking collar is slid over the surgical instrument to flex a flexible tab supporting a lock of the locking collar outward. When the loading unit is fully received on the distal end of the surgical instrument, a locking window of the loading unit becomes aligned with the lock. When this occurs, the resilience of the flexible tab causes the lock to move into the locking window to secure the loading unit to the distal end of the surgical instrument. The locking collar can be rotated about the loading unit such that the radial cam surface engages the loading unit to flex the flexible tab outwardly until the lock is removed from the locking window of the surgical instrument to release the loading unit from the distal end of the surgical instrument.

Figure 1B:
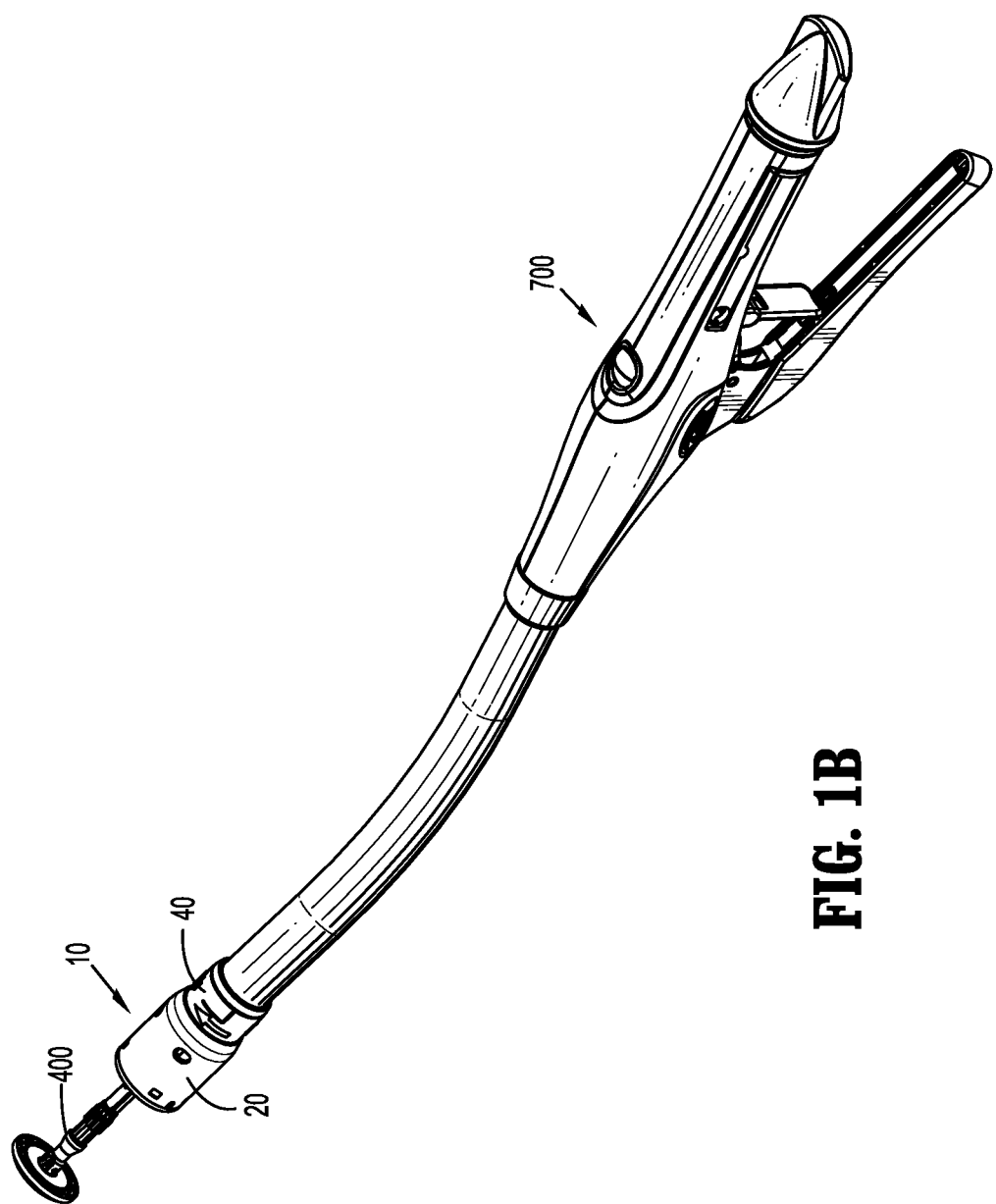
FIG. 1B is a perspective view of a circular stapling surgical instrument with the loading unit of FIG. 1A releasably coupled to a distal end of the surgical instrument.

With reference to FIGS. 1A and 1B, a loading unit 10 is provided in accordance with embodiments of the present disclosure. The loading unit 10 is configured for selective connection to a powered hand held electromechanical instrument (not shown) via an adapter 102 of a surgical instrument. Alternatively, the loading unit 10 can be configured for connection directly to a manually actuated handle assembly or stapling instrument 700 (FIG. 1B) such as described in U.S. Pat. No. 8,789,737 ("the '737 Patent"), which is incorporated herein by reference. In the illustrated embodiment, the loading unit 10 is releasably coupled to a distal end portion 110 of the adapter 102 and includes a staple cartridge 12 (FIG. 3), a shell assembly 20, and a locking collar 40. The loading unit 10 may also include an anvil 400 (FIG. 1B). The adapter 102 is configured to translate movement of an actuator of the stapling instrument, e.g., an electromechanical actuator (not shown), to actuate the shell assembly 20 to suture and cut tissue (not shown). A proximal end 104 of the adapter 102 is attachable to the stapling instrument to actuate the staple cartridge 12. It is contemplated that the proximal end 104 of the adapter 102 may be attached to a manually actuated instrument such as described in the '737 Patent to actuate the staple cartridge 12.

For a detailed description of the structure and function of an exemplary adapter and loading unit, please refer to commonly owned U.S. Provisional Patent Application Ser. No. 62/066,518, filed Oct. 21, 2014, entitled "Adapter, Extension, and Connector Assemblies for Surgical Devices." For a detailed description of the structure and function of an exemplary electromechanical instrument, please refer to commonly owned U.S. patent application Ser. No. 13/484,975, filed on May 31, 2012, now published as U.S. Patent Publication No. 2012/0253329. Each of these applications is incorporated herein by reference in its entirety.

Figure 2:
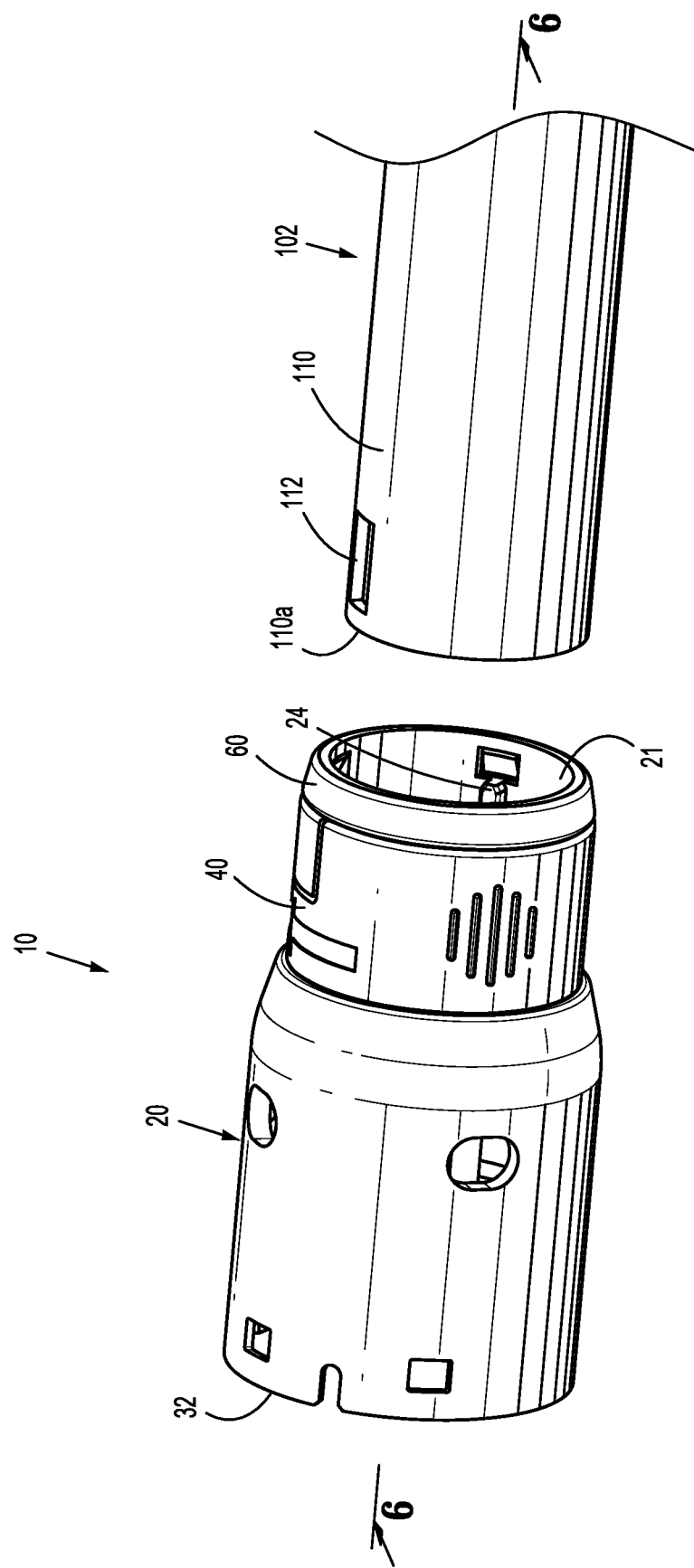
FIG. 2 is a perspective view of the adapter of FIG. 1A with the loading unit decoupled from the adapter.

Referring to FIG. 2, the distal end portion 110 of surgical instrument, e.g., the adapter 102, defines a locking window 112. The locking window 112 passes through the outer surface of the distal end portion 110 of the adapter 102 and is spaced-apart from a distal end 110a of the adapter 102. The distal end portion 110 may also define a keyway 114 (FIG. 6) that extends from the distal end 110a of the adapter 102 parallel to a longitudinal axis of the adapter 102.

Figure 3:
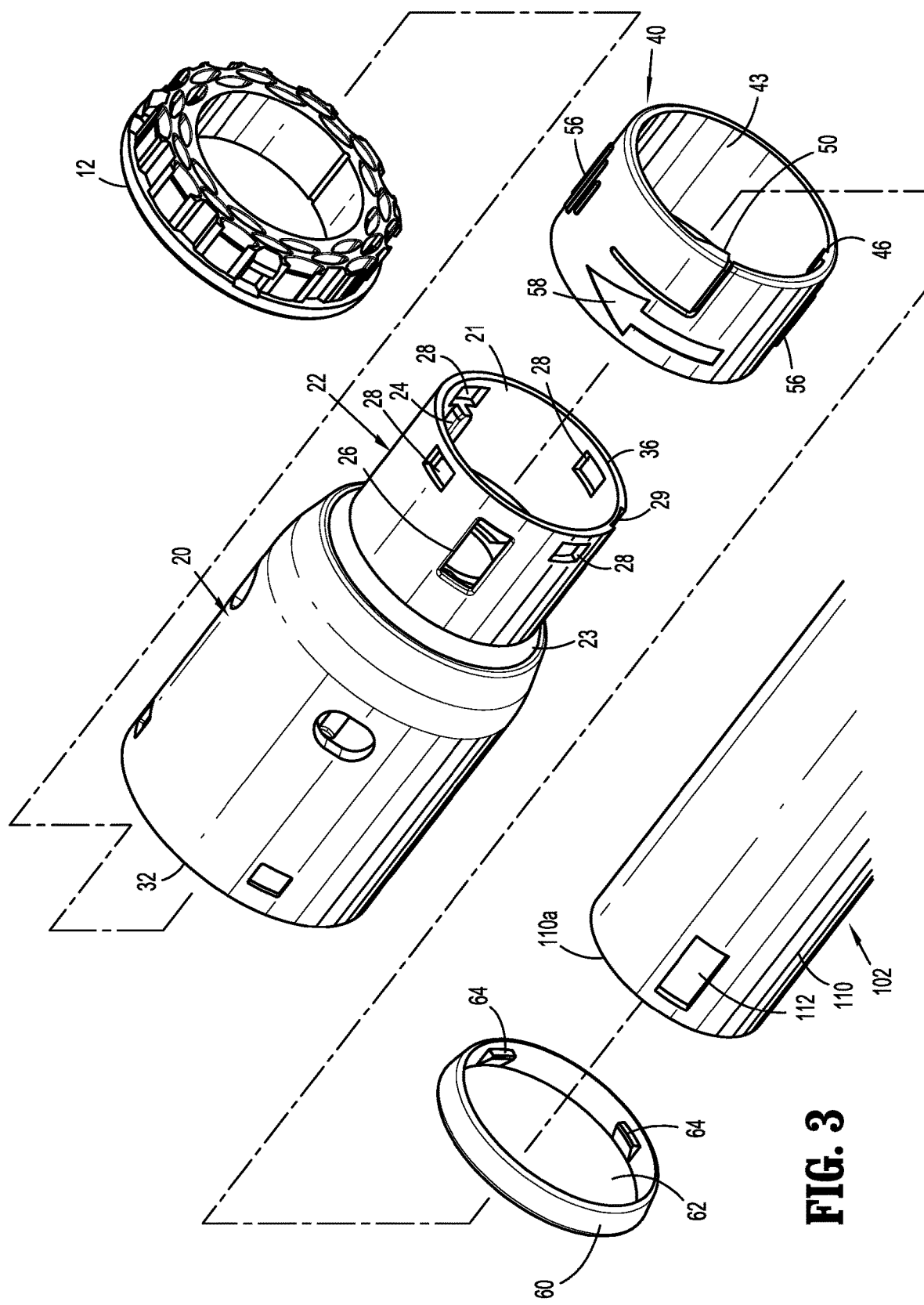
FIG. 3 is an exploded view with parts separated of the loading unit of FIG. 2.

Referring also to FIG. 3, the loading unit 10 includes a shell assembly 20, a locking collar 40, and a retention ring 60. The shell assembly 20 has a proximal recessed annular ring 22 that defines a cylindrical opening 21 for receiving the distal end portion 110 of the adapter 102 and a distal end 32 that defines a receptacle 34 (FIG. 6) for receiving and supporting the staple cartridge 12.

Figure 4:
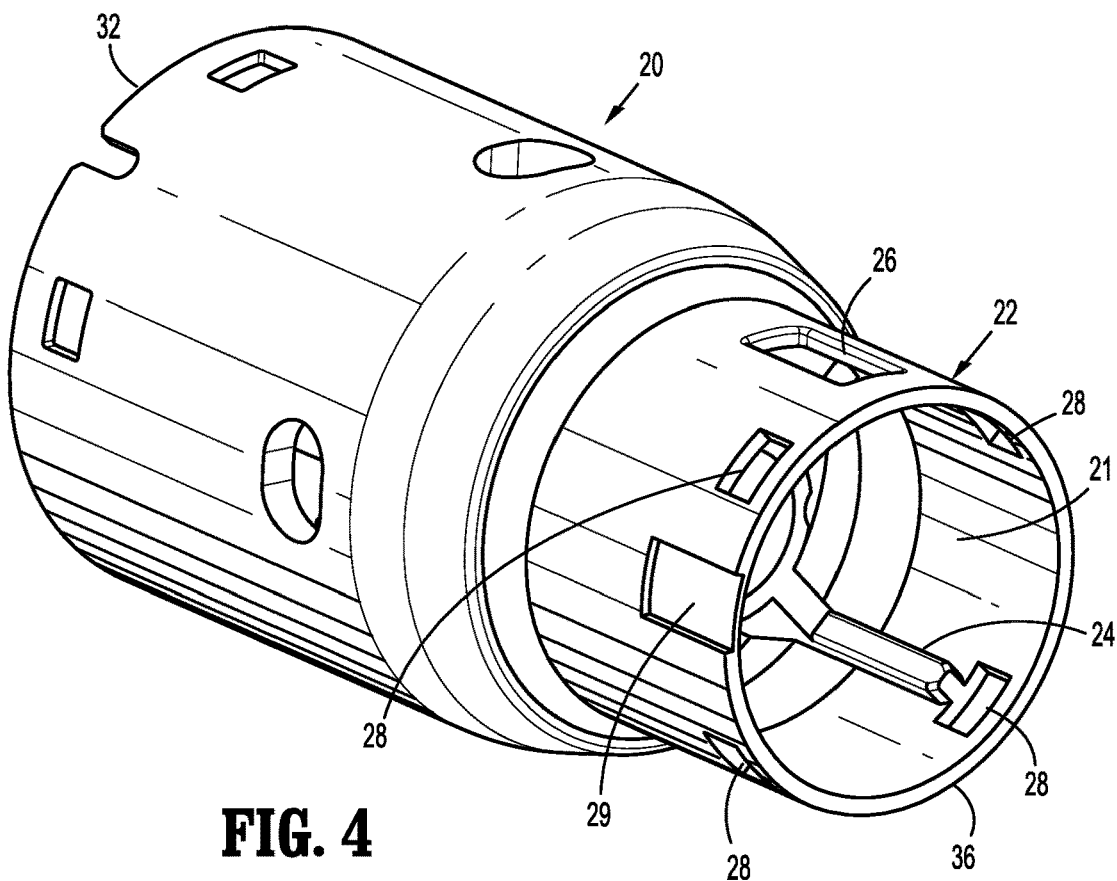
FIG. 4 is a perspective view of a shell assembly of the loading unit of FIG. 3.

Referring to FIGS. 3 and 4, the annular ring 22 of the shell assembly 20 is sized to be received through the locking collar 40 and the retention ring 60. In embodiments, the locking collar 40 has a thickness equal to the depth of a step 23 defined by the annular ring 22 such that the locking collar 40 forms a continuous or smooth surface with the outer surface of the shell assembly 20.

The annular ring 22 includes a key 24 and defines a locking slot 26 and retention slots 28. The key 24 is disposed on an inner surface of the annular ring 22 and is parallel to a longitudinal axis of the shell assembly 20. As shown, the key 24 is aligned with one of the retention slots 28; however, it is contemplated that the key 24 may be positioned between two retention slots 28.

The locking slot 26 is configured to receive a portion of the locking collar 40 to secure the shell assembly 20 to the distal end portion 110 of the adapter 102. The locking slot 26 has a substantially rectangular shape and passes between an outer surface and an inner surface of the annular ring 22. The locking slot 26 may be oriented such that the walls defining the locking slot 26 are parallel and perpendicular to the longitudinal axis of the shell assembly 20. As shown, the locking slot 26 substantially opposes the key 24. However, the locking slot 26 and the key 24 may be adjacent one another or positioned anywhere about the annular ring 22 relative to one another. The locking slot 26 is positioned between two retention slots 28 and is spaced from a proximal end 36 of the shell assembly 20 such that a proximal end of the locking slot 26 is further away from the proximal end 36 than a distal end of the retention slots 28.

The retention slots 28 are configured to receive a portion of the retention ring 60 to secure the retention ring 60 to the annular ring 22 of the shell assembly 20. As shown, the retention slots 28 are substantially rectangular in shape and are disposed about the annular ring 22. Each of the retention slots 28 are spaced an equal distance from the proximal end 36 of the shell assembly 20. As shown, the retention slots 28 are equally spaced about the annular ring 22 (i.e., at 90° apart); however, it is contemplated that the retention slots 28 may be unequally spaced about the annular ring 22 to fix the orientation of the retention ring 60 with the annular ring 22 and/or the locking collar 40. Additionally or alternatively, each of the retention slots 28 may have a unique shape to fix the orientation of the retention ring 60 with the annular ring 22 and/or the locking collar 40.

With particular reference to FIG. 4, an outer surface of the annular ring 22 defines a travel groove 29. The travel groove 29 extends from the proximal end 36 of the shell assembly 20 in a direction parallel to the longitudinal axis of the shell assembly 20. The travel groove 29 has a radial dimension about the annular ring 22 as described in greater detail below.

Figure 5:
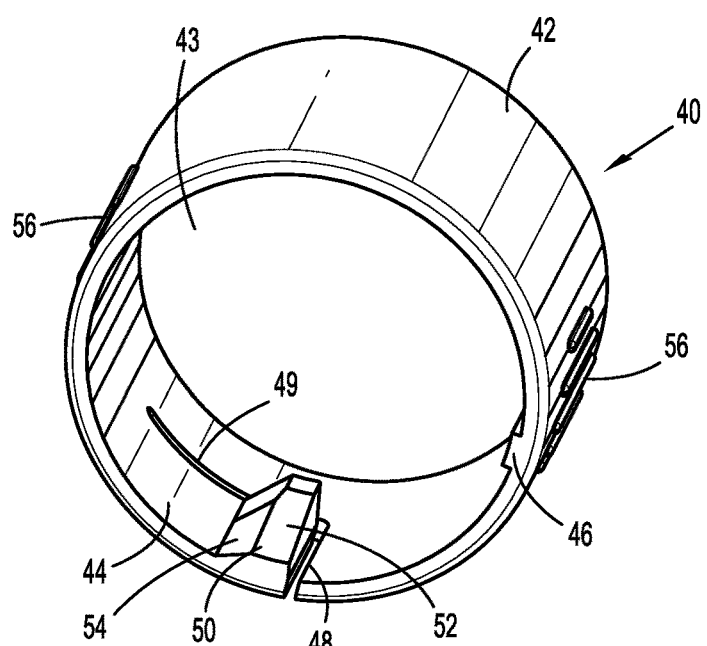
FIG. 5 is a perspective view of a locking collar of the loading unit of FIG. 3.

Referring to FIG. 5, the locking collar 40 is configured to secure the shell assembly 20 to the distal end portion 110 of the adapter 102. The locking collar 40 has a resilient, cylindrical body 42 that defines a central opening 43. The body 42 includes a flexible tab 44, a travel rib 46, and a lock 50 supported on one end of the flexible tab 44. The central opening 43 is sized to rotatably receive the annular ring 22. The diameter of the central opening 43 is slightly larger than an outer diameter of the annular ring 22 to allow rotation of the locking collar 40 about the annular ring 22 with minimal resistance (e.g., resistance from friction) and to prevent excessive movement relative to the annular ring 22 due to an excess gap between the body 42 and the annular ring 22. The flexible tab 44 defines a cantilever and is formed by partially splitting the body 42 with a radial slit 48 and a longitudinal slit 49. The tab 44 may have a width that is approximately half the width of the body 42 and has a radial dimension in a range of about 45° to about 90° (e.g., about 75°). Alternatively, other configurations are envisioned.

The lock 50 is disposed on an inner surface of the tab 44 adjacent the longitudinal slit 49 and extends into the central opening 43 of the locking collar 40. The lock 50 includes a longitudinal cam 52 and a radial cam 54. The longitudinal cam 52 is an angled surface that extends from a proximal side of the lock 50 towards a distal side of the lock 50 and towards the center of the central opening 43 to form a proximally facing wedge. The radial cam 54 is an angled surface that extends from a side of the lock 50 spaced apart from the longitudinal slit 49 and angles away from the flexible tab towards the longitudinal slit 49 and the center of the central opening 43 to form a radial wedge facing away from the longitudinal slit 49.

The travel rib 46 extends inward from the inner surface of the body 46 and is positioned adjacent the proximal end of the body 42. The travel rib 46 extends approximately halfway across the inner surface of the body 46 but may extend from the proximal end to the distal end of the body 42. The travel rib 46 is sized to be received within the travel groove 29 when the locking collar 40 is disposed about the annular ring 22 to limit rotation of the locking collar 40 about the annular ring 22 as discussed in greater detail below.

Referring briefly back to FIGS. 2 and 3, the retention ring 60 is configured to retain the locking collar 40 over the annular ring 22 (i.e., prevent the locking collar 40 from proximally translating off of the annular ring 22). The retention ring 60 defines a central opening 62 and includes retention tabs 44. The central opening 62 is sized to receive the annular ring 22. The retention tabs 64 are disposed about the inner surface of the retention ring 60 and include distally facing wedges that are configured to be received within the retention slots 28 of the annular ring 22 to radially fix the retention ring 60 to the annular ring 22 and to prevent the retention ring 60 from proximal translation relative to the annular ring 22. More specifically, when the retention ring 60 is slid over the annular ring 22, tapered surfaces of the retention tabs 64 engage a distal surface or the annular ring 22 such that the tabs 64 are deformed inwardly and pass over the annular ring 22 until the tabs 64 become aligned with the retention slots 28. When the tabs 64 become aligned with the slots 28, the tabs 64, which are resilient, spring outwardly into the retention slots 28 to secure the retention ring 60 about the annular ring 22. It is contemplated that the retention tabs 64 may also prevent distal translation of the retention ring 60 relative to the annular ring 22. The outer surface of the retention ring 60 may slope proximally to provide a smooth transition from the outer surface of the shell assembly 20 to the distal end portion 110 of the adapter 102 when the distal end portion 110 is received within the proximal opening 21 of the shell assembly 20.

Referring to FIGS. 3 and 6-8, the assembly of the adapter 102 and the shell assembly 20 of the loading unit 10 with the locking collar 40 will be described in accordance with the present disclosure. As shown in FIG. 3, the shell assembly 20 and the locking collar 40 are aligned with one another such that the longitudinal axis of the shell assembly 20 is aligned with the longitudinal axis of the locking collar 40. In addition, the locking collar 40 is rotationally aligned with the annular ring 22 of the shell assembly 20 by aligning the travel rib 46 of the locking collar 40 with the travel groove 29 of the annular ring 22. It will be appreciated that when the travel rib 46 and the travel groove 39 are rotationally aligned, the lock 50 of the locking collar 40 is substantially aligned with the locking slot 26 of the annular ring 22.

With the locking collar 40 and the annular ring 22 of the shell assembly 20 aligned with one another, the locking collar 40 is moved distally over the annular ring 22 such that the annular ring 22 is received within the central opening 43 of the locking collar 40. As the locking collar 40 is moved over the annular ring 22, the lock 50 engages the annular ring 22. Continued distal movement of the locking collar 40 over the annular ring 22 flexes the flexible tab 44 of the locking collar 40 outward such that the lock 50 of the flexible tab 44 is positioned to move along the outer surface of the annular ring 22. With the lock 50 positioned on the outer surface of the annular ring 22, the locking collar 40 is moved distally over the annular ring 22 until a distal end of the locking collar 40 abuts the step 23 defined by the annular ring 22. In this position, the lock 50 is positioned in alignment with the locking slot 26. When the distal end of the locking collar 40 abuts the step 23 as shown in FIG. 6, the resilience of the flexible tab 44 moves the lock 50 towards the longitudinal axis of the shell assembly 20 and through the locking slot 26 of the annular ring 22 to secure the locking collar 40 to the shell assembly 20 about the annular ring 22.

Figure 6:
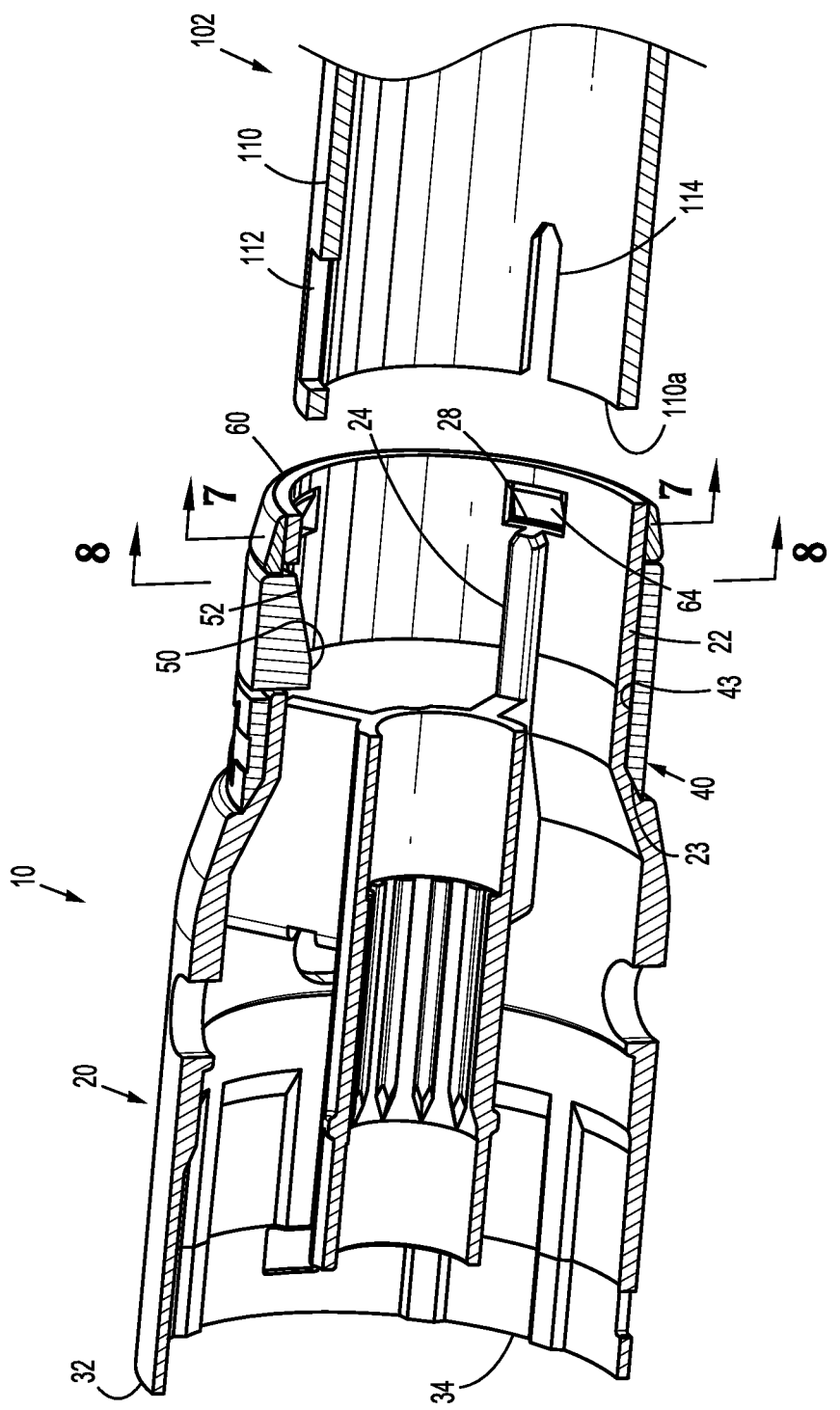
FIG. 6 is a longitudinal cross-sectional view of the loading unit and the distal end portion of the adapter taken along the section line 6-6 of FIG. 2.
Figure 8:
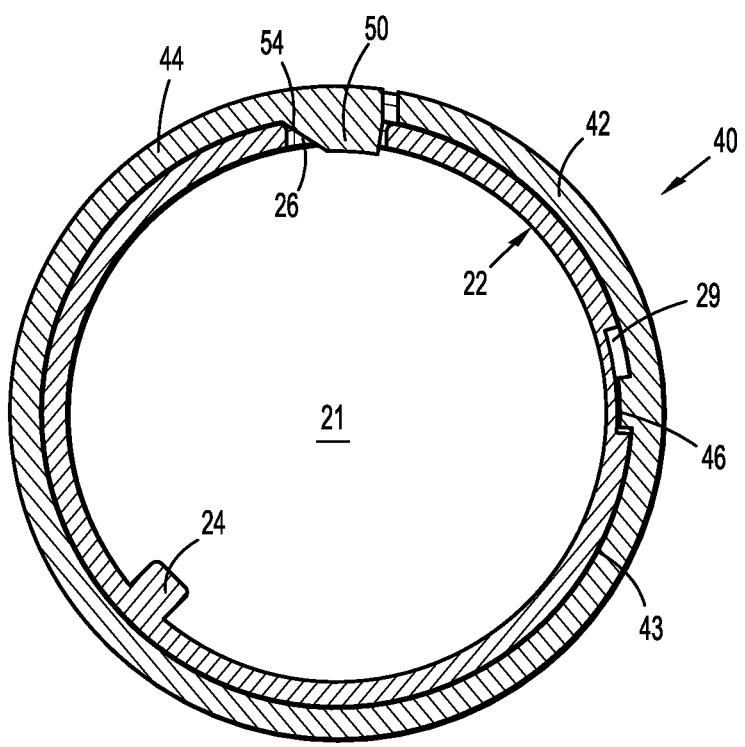
FIG. 8 is a cross-sectional view taken along the section line 8-8 of FIG. 6.

If the locking collar 40 is slightly misaligned with the locking slot 26 with the lock 50 extending partially through the locking slot 26 of the annular ring 22, the first or longitudinal cam surface 52 of the lock 50 engages walls defining the locking slot 26 to distally slide the locking collar 40 over the annular ring 22 and the second or radial cam surface 54 of the lock 50 engages the walls defining the locking slot 26 to rotate the locking collar 40 about the annular ring 22 to a locked configuration as shown in FIGS. 6 and 8. In the locked configuration, resilience of the flexible tab 44 urges the lock 50 through the locking slot 26 such that the lock 50 prevents rotation of the locking collar 40 about the annular ring 22 and translation of the locking collar 40 relative to the annular ring 22. In the locked configuration, the travel rib 46 of the locking collar 40 is positioned on one side of the travel groove 29 such that the travel rib 46 prevents rotation of the locking collar 40 about the annular ring 22 in a first direction (e.g., clockwise as shown in FIG. 8) and allows rotation of the locking collar 40 in a second direction opposite the first direction (e.g., counter clockwise as shown in FIG. 8). When the locking collar 40 reaches the locked configuration, the flexible tab 44 may provide audible indicia (e.g., a click) as the lock 50 passes through the locking slot 26.

Figure 7:
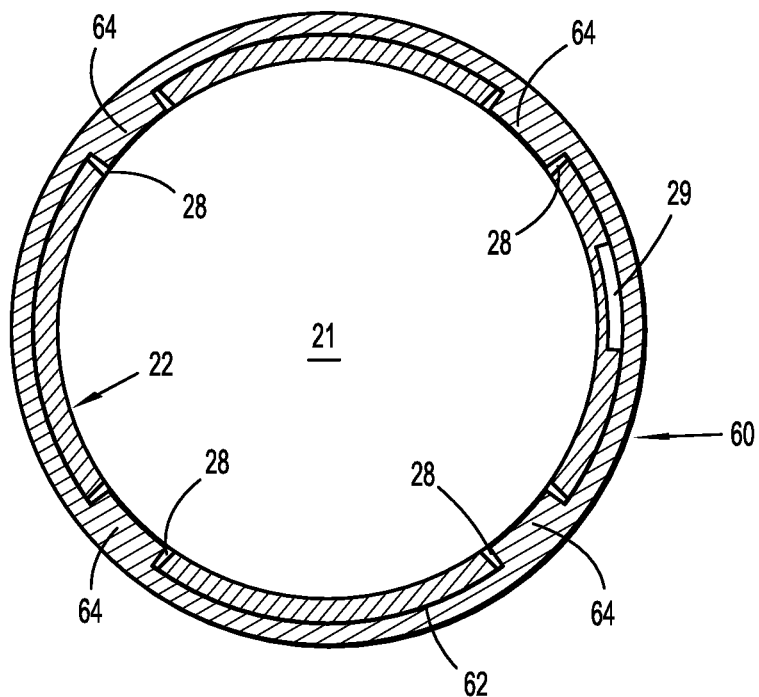
FIG. 7 is a cross-sectional view taken along the section line 7-7 of FIG. 6.

With particular reference to FIGS. 6 and 7, the retention ring 60 is secured over a proximal end of the annular ring 22 proximal to the locking collar 40 to prevent the locking collar 40 from sliding proximally relative to the annular ring 22. With the locking collar 40 in the locked configuration, the retention ring 60 is slid distally over the annular ring 22 such that the annular ring 22 is received within the central opening 62 of the retention ring 60. As the retention ring 60 receives the annular ring 22, the retention tabs 64 engage the outer surface of the annular ring 22 and flex outwardly such that the retention ring 60 can pass over the annular ring 22. The retention ring 60 is positioned about the annular ring 22 such that each retention tab 64 is positioned within one of the retention slots 28 of the annular ring 22. As the retention tabs 64 are aligned with the retention slots 28, the resilience of the retention ring 60 urges the retention tabs 64 through the retention slots 28 such that the retention ring 60 is in a fixed configuration relative to the annular ring 22. When the retention ring 60 reaches the fixed configuration, the passage of the retention tabs 64 through the retention slots 28 of the retention ring 60 may provide audible indicia (e.g., a click). In the fixed configuration of the retention ring 60, the retention ring 60 is rotationally and longitudinally fixed relative to the annular ring 22. Further, in the fixed configuration, the retention ring 60 prevents the locking collar 40 from sliding proximally off the annular ring 22 of the shell assembly 20 but allows the locking collar 40 to rotate about the annular ring 22.

Each retention tab 64 is disposed within a respective retention slot 28; however, it is contemplated that each retention slot 28 may not receive a retention tab 64. As shown, the retention tabs 64 and the retention slots 28 are equally spaced about the retention ring 60 and the annular ring 22 respectively; however, it is contemplated that the retention tabs 64 and the retention slots 28 may be unequally spaced about the retention ring 60 and the annular ring 22 respectively to define a radial orientation of the retention ring 60 relative to the annular ring 22. The loading unit 10 is assembled when the locking collar 40 is in the locked configuration and the retention ring 60 is in the fixed configuration.

With reference to FIGS. 6 and 9-14, a method for securing the loading unit 10 to the distal end portion 110 of the adapter 102 or surgical instrument is disclosed in accordance with the present disclosure. Referring initially to FIG. 6, assembled loading unit 10 is aligned with the distal end portion 110 of the adapter 102 such that the longitudinal axis of the loading unit 10 is aligned with the longitudinal axis of the adapter 102. The loading unit 10 is then radially aligned with the distal end portion 110 of the adapter 102 such that the key 24 of the shell assembly 22 is aligned with the keyway 114 of the distal end portion 110 as shown in FIG. 6. When the key 24 and the keyway 114 are radially aligned, the locking slot 26 of the shell assembly 22 is radially aligned with the lock window 112 of the distal end portion 110 of the adapter 102.

Figure 9:
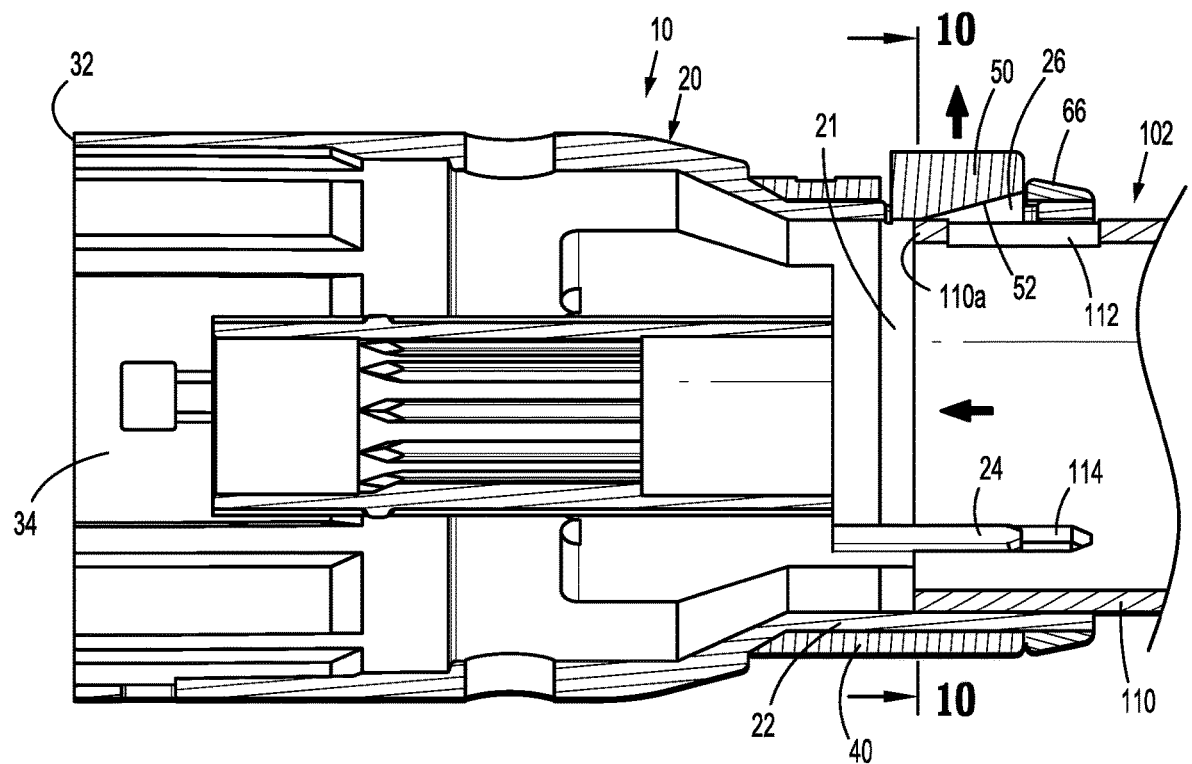
FIG. 9 is a longitudinal cross-sectional view of the distal end portion of the adapter of FIG. 2 partially received within an annular ring of the loading unit of FIG. 2.
Figure 10:
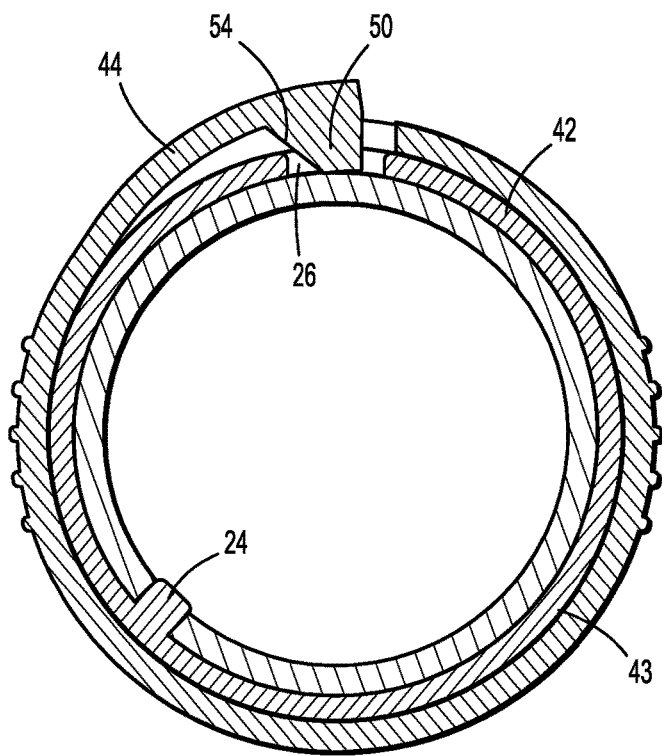
FIG. 10 is a cross-sectional view taken along the section line 10-10 of FIG. 9.
Figure 11:
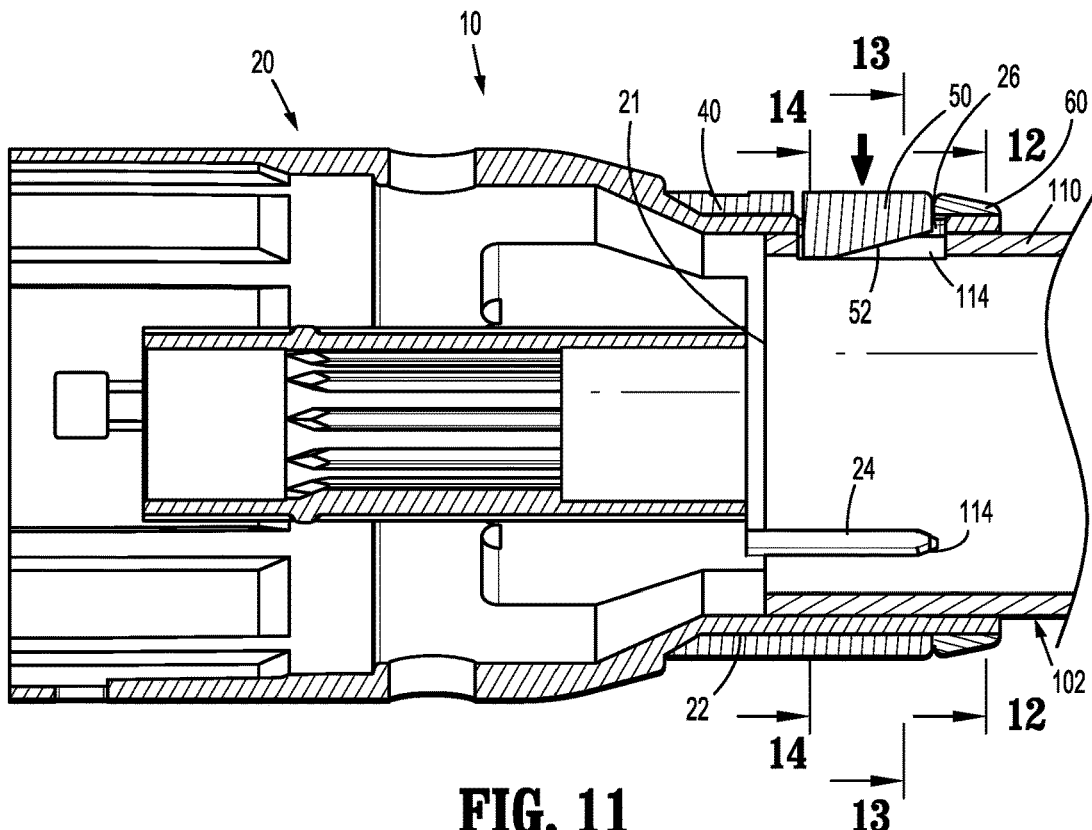
FIG. 11 is a longitudinal cross-sectional view of the distal end portion of the adapter of FIG. 2 received within an annular ring of the loading unit of FIG. 2.
Figure 12:
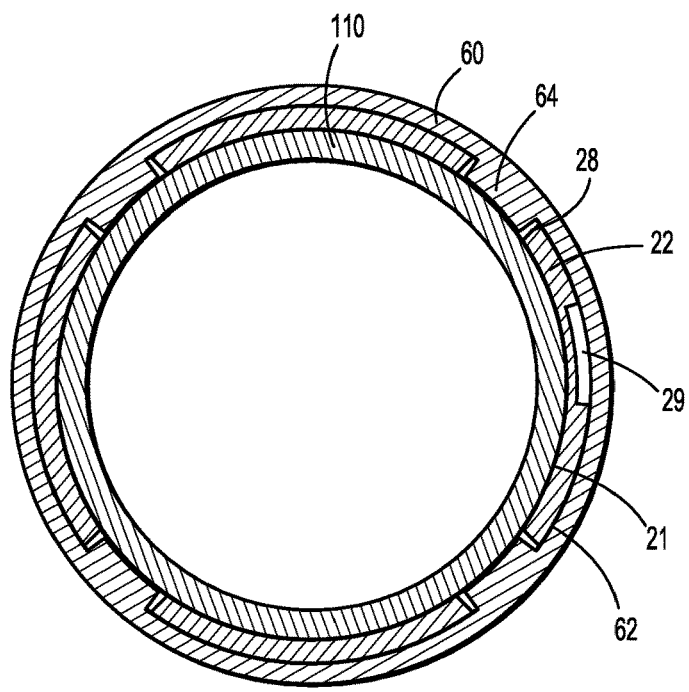
FIG. 12 is a cross-sectional view taken along the section line 12-12 of FIG. 11.
Figure 13:
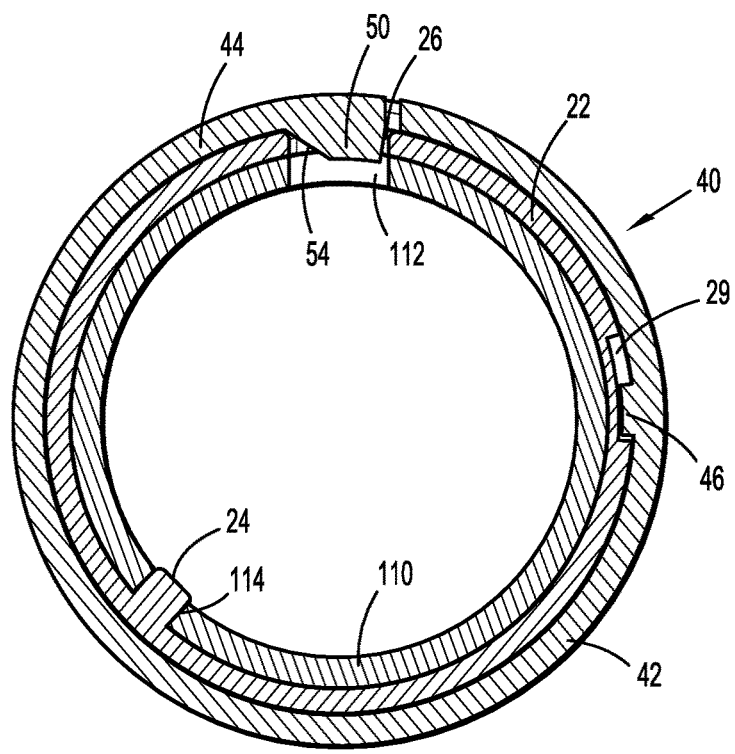
FIG. 13 is a cross-sectional view taken along the section line 13-13 of FIG. 11.
Figure 14:
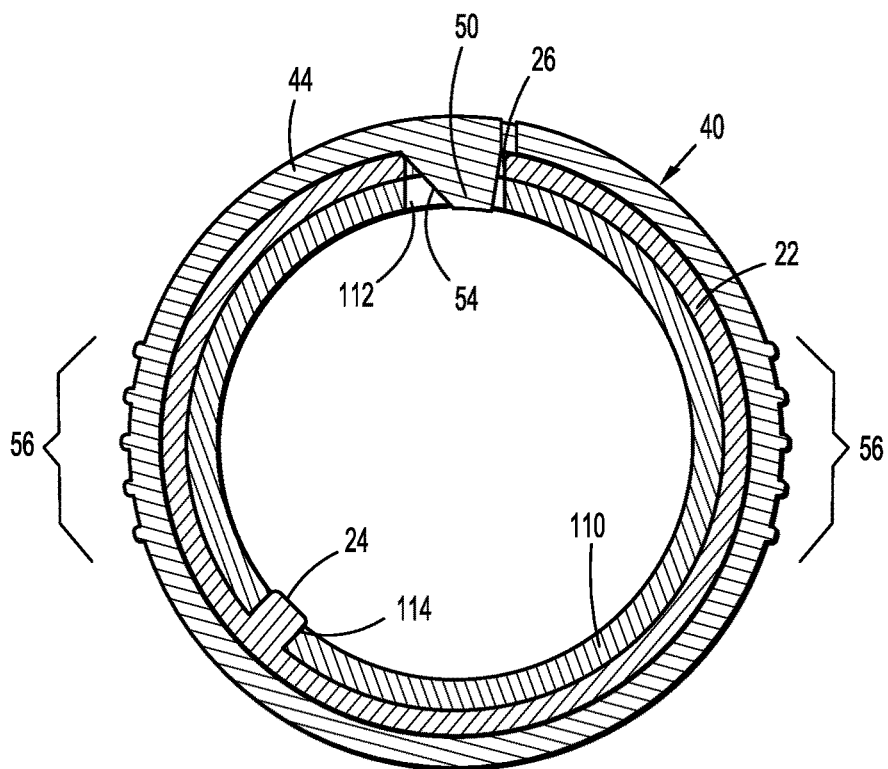
FIG. 14 is a cross-sectional view taken along the section line 14-14 of FIG. 11.
Figure 15:
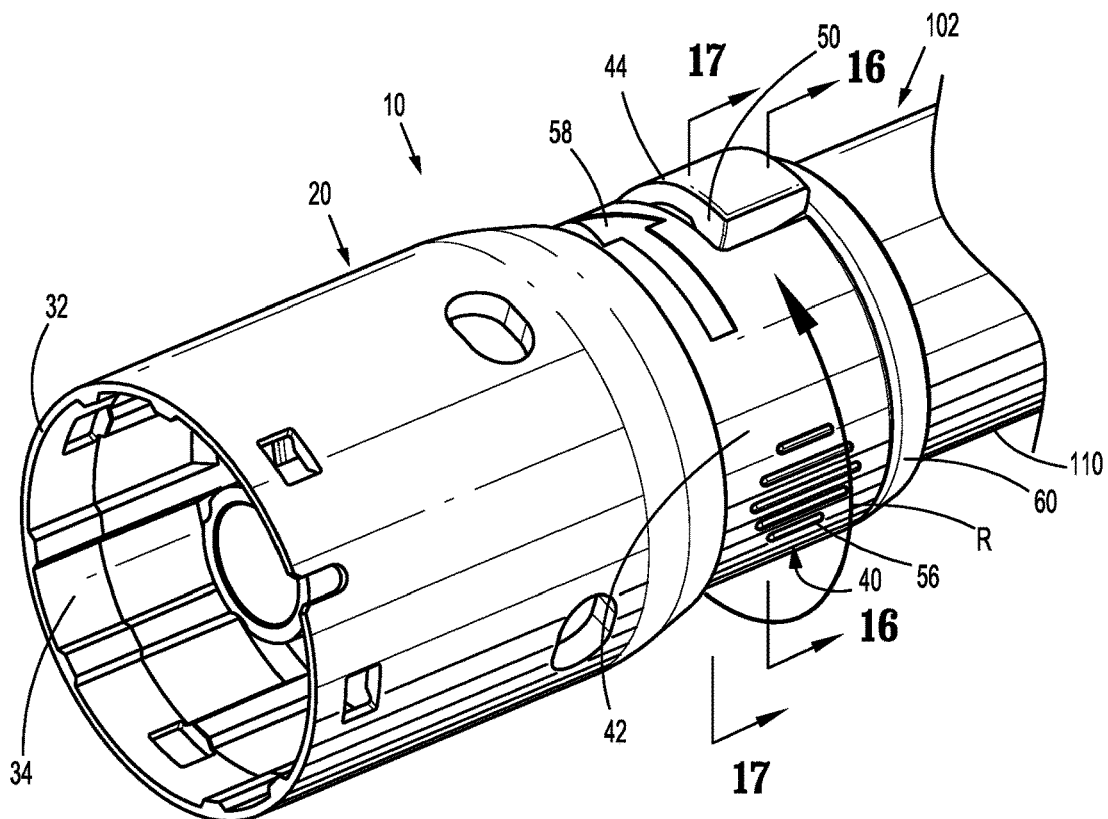
FIG. 15 is a perspective view of the loading unit of FIG. 2 disposed over the distal end portion of the adapter with the locking collar rotated to an unlocked configuration.

Referring now to FIGS. 9 and 10, with the loading unit 10 and the distal end portion 110 of the adapter 102 aligned with one another, the loading unit 10 is slid over the distal end portion 110 of the adapter 102 such that the distal end portion 110 of the adapter 102 is at least partially disposed within the proximal opening 21 of the shell assembly 20. As the distal end portion 110 of the adapter 102 slides into the proximal opening 21, the key 24 slides in the keyway 114 of the distal end portion 110. Further, as the distal end portion 110 of the adapter 102 slides into the proximal opening 21, the distal end 110a of the adapter 102 adjacent the locking slot 112 engages the lateral cam surface 52 of the lock 50 to urge the lock 50 and the flexible tab 40 outward. The loading unit 10 is slid over the distal end portion 110 of the adapter 102 until the lock window 112 of the adapter 102 is longitudinally aligned with the locking slot 26 of the annular ring 22 of the shell assembly 20. When lock window 112 and the locking slot 26 are aligned, the resilience of the flexible tab 44 urges or snaps the lock 50 through the lock window 112 of the adapter 102 and into the locked configuration as shown in FIG. 11. When the lock 50 reaches the locked configuration, the lock 50 may provide audible indicia (e.g., a click) to a user.

As shown in FIGS. 11-14, the loading unit 10 is secured to the distal end portion 110 of the adapter 102 when the distal end portion 110 of the adapter 102 is positioned within the proximal opening 21 of the shell assembly 20 with the lock 50 disposed in the lock window 112 in the locked configuration. With the loading unit 10 secured to the distal end portion 110 of the adapter 102, the surgical instrument and loading unit 10 may be used to perform a surgical procedure. After surgical procedure is completed, the loading unit 10 can be decoupled or detached from the surgical instrument as will be discussed in detail below. With the loading unit 10 decoupled from the surgical instrument, another loading unit may be coupled or secured to the surgical instrument for continued use in the surgical procedure, the surgical instrument may be sterilized for use in another surgical procedure, or the surgical instrument may be discarded. In addition, the loading unit 10 may be sterilized for use in another surgical procedure or may be discarded.

Figure 16:
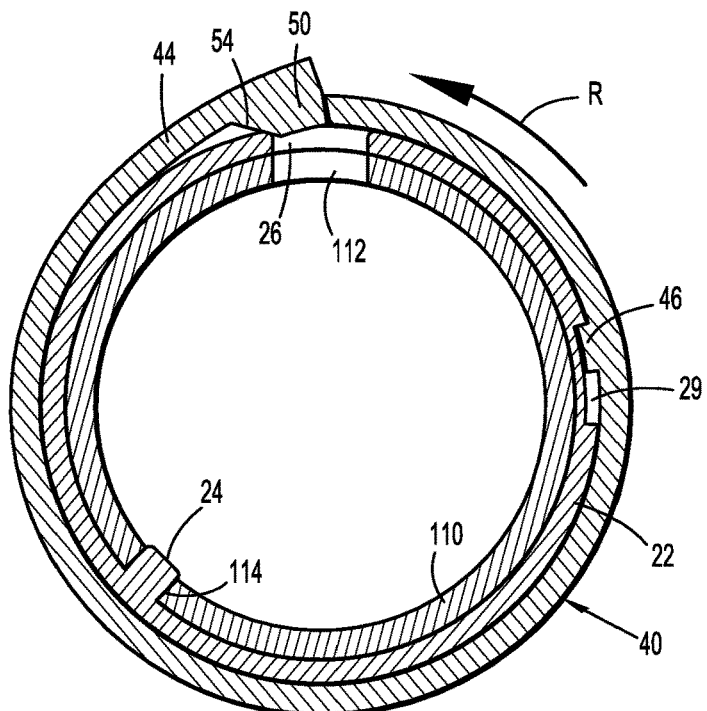
FIG. 16 is a cross-sectional view taken along the section line 16-16 of FIG. 15.
Figure 17:
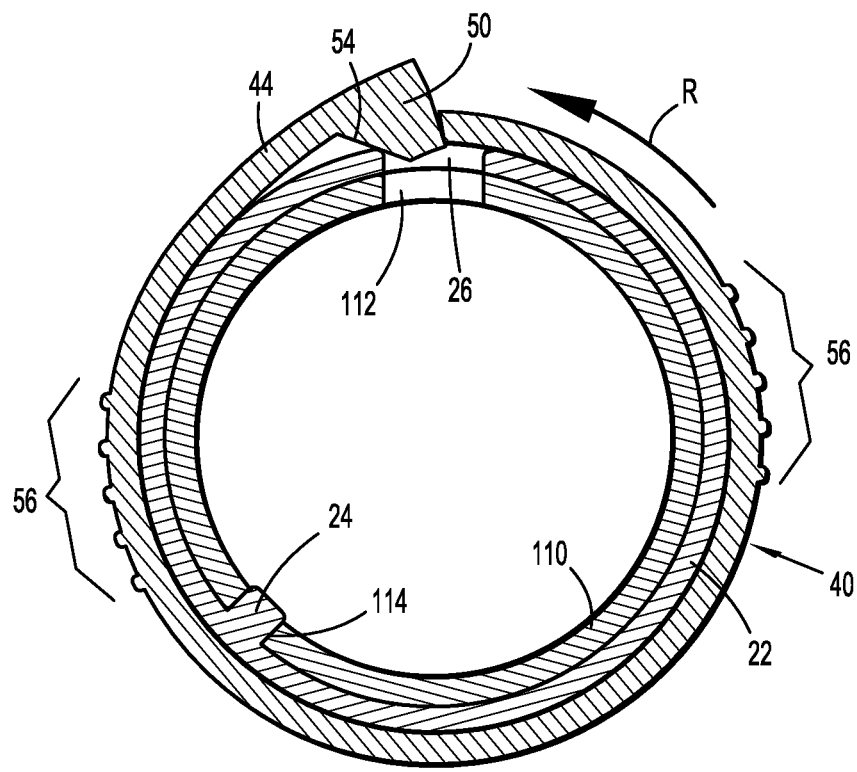
FIG. 17 is a cross-sectional view taken along the section line 17-17 of FIG. 15.
Figure 18:
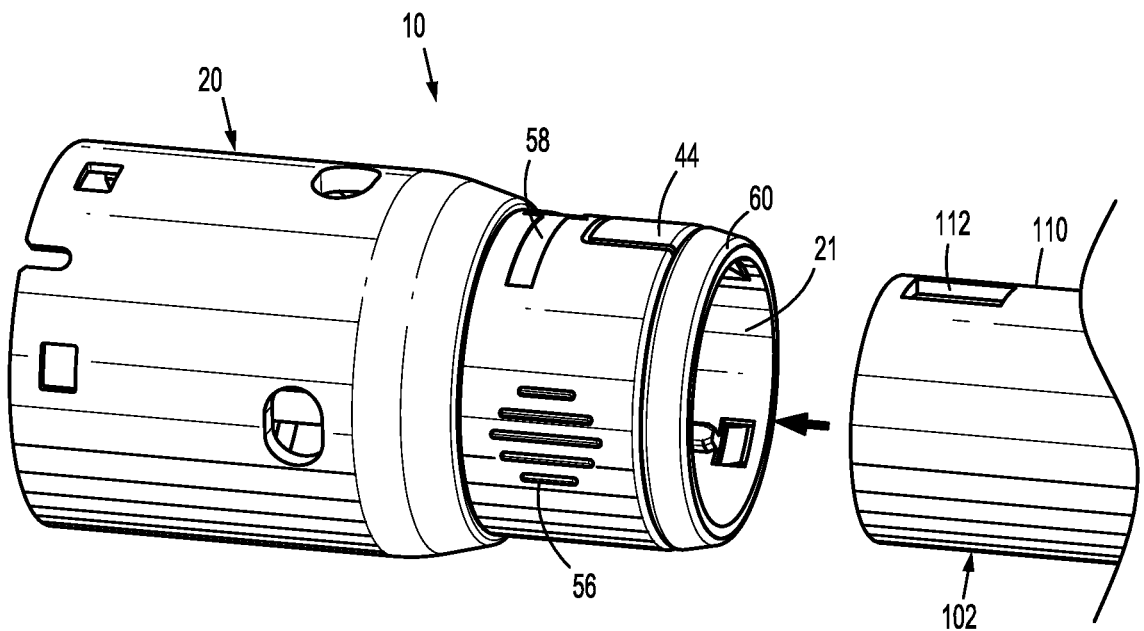
FIG. 18 is a perspective view of the loading unit of FIG. 15 released from the distal end portion of the adapter with the locking collar returned to the locked configuration.

With reference to FIGS. 15-18, a method for detaching the loading unit 10 from the distal end portion 110 of the adapter 102 or surgical instrument is disclosed in accordance with the present disclosure. To detach the loading unit 10, the body 42 of the locking collar 40 is rotated about the annular ring 22 of the shell assembly 20 such that the lock 50 is moved outward and from within of the lock window 112 of the adapter 102 to release the distal end portion 110 of the adapter 102 from the loading unit 10. Specifically, the body 42 of the locking collar 40 is rotated about the annular ring 22 in the direction indicated by arrow "R". The outer surface of the body 42 may include engagement features 56 to provide a clinician a grip for rotating the body 42. With particular reference to FIGS. 16 and 17, as the body 42 is rotated in the direction of arrow "R", the second cam surface 54 of the lock 50 engages the walls defining the locking slot 36 to move or cam the lock 50 outward to an unlocked configuration. When the lock 50 is in the unlocked configuration, the loading unit 10 is distally slidable to release or detach the distal end portion 110 of the adapter 102 from the loading unit 10 as shown in FIG. 18. When the loading unit 10 is detached from the distal end portion 110, the body 42 is released such that the resilience of the body 42 and the flexible tab 44 return the locking collar 40 to the locked configuration.

As the body 42 of the locking collar 40 is rotated about the distal end portion 110 of the adapter 102, the key 24 and the keyway 114 prevent the shell assembly 20 from rotating relative to the adapter 102. Further, as detailed above, the retention tabs 64 and the retention slots 28 prevent the retention ring 60 from rotating about the shell assembly 20.

With particular reference to FIG. 16, the travel rib 46 prevents over rotation of the body 42 of the locking collar 40 about the annular ring 22. Specifically, as the body 42 is rotated about the annular ring 22, the travel rib 46 moves from the fixed configuration (FIG. 13) to a released configuration within the travel groove 29 as shown in FIG. 16. When the travel rib 46 is in the released configuration, the lock 50 is outside of the lock window 112 of the adapter 102 and may be substantially out of the locking slot 26 of the annular ring 22. The travel rib 46 prevents over rotation of the body 42 about the annular ring 22 to a point where the resilience of the body 42 is unable to return the lock 50 to the locked configuration.

The locking collar 40 is made of a resilient material. For example, the locking collar 12 may be formed of a resilient plastic material using an injection molding process. However, it is contemplated the locking collar 40 may be formed of other suitable materials including, but not limited to, spring steel, stainless steel, or wire.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. The present disclosure is not limited to circular stapling loading units, but has application to loading units for linear stapling or other types of instruments, such as electrocautery or ultrasonic instruments.

Therefore, the above description should not be construed as limiting, but merely as exemplifications of particular embodiments. Those skilled in the art will envision other modifications within the scope of the claims appended hereto.

What is claimed:

1. A loading unit comprising:
   a shell assembly having an annular ring defining a proximal opening configured to receive a distal end portion of a surgical instrument, the annular ring defining a locking slot;
   a staple cartridge supported on the shell assembly; and
   a locking collar rotatably disposed about the annular ring, the locking collar having a body including a flexible tab, the flexible tab having a lock extending inwardly from the flexible tab, the lock having a longitudinal cam surface defining a proximally facing wedge and a radial cam surface defining a radial wedge, the locking collar being moveable about the annular ring between a locked configuration wherein the lock passes through the locking slot and into the proximal opening of the annular ring and an unlocked configuration wherein the lock is moved from within the proximal opening.

2. The loading unit according to claim 1, wherein the body is partially split to form the flexible tab.

3. The loading unit according to claim 1, wherein an outer surface of the annular ring defines a groove and the locking collar includes an inwardly extending travel rib that is received within the groove.

4. The loading unit according to claim 3, wherein the travel rib limits a degree of rotation of the locking collar about the annular ring.

5. The loading unit according to claim 1, further comprising a retention ring positioned about the annular ring proximal of the locking collar to prevent axial movement of the locking collar relative to the annular ring.

6. The loading unit according to claim 5, wherein the retention ring includes a plurality of inwardly extending retention tabs and the annular ring defines a plurality of retention slots positioned proximally of the locking slot, each of the plurality of retention slots being configured to receive a respective retention tab to fix the retention ring to the annular ring.

7. The loading unit according to claim 1, wherein the flexible tab is resilient and is positioned to urge the locking collar to the locked configuration.

8. The loading unit according to claim 7, wherein the lock has a longitudinal cam surface and a radial cam surface.

9. The loading unit according to claim 8, wherein the radial cam surface is positioned to engage the annular ring to move the lock outward in response to rotation of the body of the locking collar in relation to the annular ring towards the unlocked configuration.

10. The loading unit according to claim 8, wherein the radial cam surface is positioned to engage the annular ring, wherein resiliency of the flexible tab causes the radial cam surface to urge the locking collar towards the locked configuration when the lock and the locking slot are misaligned.

11. A surgical system comprising:
a surgical instrument including a distal end portion that defines a locking window;
a loading unit including a shell assembly having an annular ring defining a proximal opening, the distal end portion of the surgical instrument received within the proximal opening, the annular ring defining a locking slot; and
a locking collar rotatably disposed about the annular ring to secure the loading unit to the distal end portion of the surgical instrument, the locking collar having a body including a flexible tab, the flexible tab having a lock extending inward from the flexible tab, the locking collar being moveable about the annular ring between a locked configuration wherein the lock passes through the locking slot of the annular ring and the locking window of the distal end portion of the surgical instrument to secure the locking collar to the distal end portion of the surgical instrument and an unlocked configuration wherein the lock is moved from within the locking window to release the loading unit from the distal end portion of the surgical instrument.

12. The surgical system according to claim 11, wherein the annular ring includes a key extending into the proximal opening, and wherein the distal end portion of the surgical instrument defines a keyway, the key parallel to a longitudinal axis of the shell assembly, the keyway parallel to a longitudinal axis of the distal end portion of the surgical instrument, the key received within the keyway to rotatably fix the loading unit to the distal end portion of the surgical instrument.

13. The surgical system according to claim 11, wherein the lock has a longitudinal cam surface, a distal end of the surgical instrument configured to engage the longitudinal cam surface to move the lock outward as the distal end portion of the surgical instrument is received within the proximal opening until the locking window is aligned with the locking slot of the annular ring.

14. The surgical system according to claim 11, wherein the lock has a radial cam surface, the radial cam surface engaging the annular ring in response to rotation of the body of the locking collar about the annular ring to transition the locking collar to the unlocked configuration.

15. The loading unit according to claim 1, further comprising a staple cartridge having a plurality of staples, the staple cartridge received within the shell assembly.

16. The surgical system according to claim 11, further comprising a staple cartridge having a plurality of staples, the staple cartridge received within the shell assembly.

* * * * *